(12) United States Patent
Ussar et al.

(10) Patent No.: US 9,446,096 B2
(45) Date of Patent: Sep. 20, 2016

(54) GLYPICAN-4 BASED COMPOSITIONS AND METHODS FOR TREATING AND DIAGNOSING INSULIN RESISTANCE

(71) Applicant: Joslin Diabetes Center, Inc., Boston, MA (US)

(72) Inventors: Siegfried Ussar, Boston, MA (US); C. Ronald Kahn, West Newton, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 0 days.

(21) Appl. No.: 14/369,095

(22) PCT Filed: Dec. 31, 2012

(86) PCT No.: PCT/US2012/072310
§ 371 (c)(1),
(2) Date: Jun. 26, 2014

(87) PCT Pub. No.: WO2013/102209
PCT Pub. Date: Jul. 4, 2013

(65) Prior Publication Data
US 2014/0364363 A1 Dec. 11, 2014

Related U.S. Application Data

(60) Provisional application No. 61/581,836, filed on Dec. 30, 2011.

(51) Int. Cl.
*A61K 38/17* (2006.01)
*C07K 14/00* (2006.01)
*A61P 5/50* (2006.01)
*G01N 33/68* (2006.01)

(52) U.S. Cl.
CPC ....... *A61K 38/1709* (2013.01); *G01N 33/6893* (2013.01)

(58) Field of Classification Search
CPC ............. A61K 38/1709; G01N 33/6893
See application file for complete search history.

(56) References Cited

U.S. PATENT DOCUMENTS

| | | | |
|---|---|---|---|
| 6,306,613 B1 | 10/2001 | Florkiewicz et al. |
| 7,196,165 B2 | 3/2007 | Ashkenazi et al. |
| 2006/0121041 A1 | 6/2006 | Friedman et al. |
| 2009/0203602 A1 | 8/2009 | Gelber et al. |
| 2009/0220973 A1 | 9/2009 | Gesta et al. |
| 2009/0298771 A1 | 12/2009 | Onichtchouk |
| 2011/0111404 A1 | 5/2011 | Salonen et al. |

FOREIGN PATENT DOCUMENTS

| | | | | |
|---|---|---|---|---|
| EP | 0925790 A1 * | 6/1999 | ........... A61K 33/334 |
| WO | 2004003179 A1 | 1/2004 | |
| WO | WO 2004/032924 A1 * | 4/2004 | ......... A61K 31/4375 |

OTHER PUBLICATIONS

Machine translation of WO 2004/032924 A1, pp. 1-4, accessed Jul. 30, 2015.*
Diabetes Mellitus, from http://www.merckmanuals.com/professional/endocrine-and-metabolic-disorders/diabetes-mellitus-and-disorders-of-carbohydrate-metabolism/diabetes-mellitus-dm, pp. 1-34, accessed Jul. 31, 2015.*
Gesta, et al., "Evidence for a role of developmental genes in the origin of obesity and body fat distribution" PNAS; Apr. 25, 2006; vol. 103; No. 17; pp. 6676-6681.
Ussar, et al., "Glypican-4 enhances insulin signaling via interaction with the insulin receptor and serves as a novel adipokine" Diabetes Journal; Sep. 2012; vol. 61; pp. 2289-2298.

* cited by examiner

*Primary Examiner* — Julie Ha
*Assistant Examiner* — Li Ni Komatsu
(74) *Attorney, Agent, or Firm* — Pierce Atwood LLP; Kevin M. Farrell; David J. Wilson

(57) ABSTRACT

Provided herein are methods for increasing insulin sensitivity in a subject. A method may comprise administering to a subject in need of increased insulin sensitivity a therapeutically effective amount of a glypican-4 agent. Also provided herein are methods for determining whether a subject is or is likely to become insulin resistant. A method may comprise determining the level of glypican-4 in a subject, wherein an elevated level of glypican-4 indicates that a subject is or is likely to become insulin resistant.

10 Claims, 18 Drawing Sheets

Human Glypican-4 precursor protein:

```
  1  MARFGLPALL CTLAVLSAAL LAAELKSKSC SEVRRLYVSK GFNKNDAPLH EINGDHLKIC
 61  PQGSTCCSQE MEEKYSLQSK DDFKSVVSEQ CNHLQAVFAS RYKKFDEFFK ELLENAEKSL
121  NDMFVKTYGH LYMQNSELFK DLFVELKRYY VVGNVNLEEM LNDFWARLLE RMFRLVNSQY
181  HFTDEYLECV SKYTEQLKPF GDVPRKLKLQ VTRAFVAART FAQGLAVAGD VVSKVSVVNP
241  TAQCTHALLK MIYCSHCRGL VTVKPCYNYC SNIMRGCLAN QGDLDFEWNN FIDAMLMVAE
301  RLEGPFNIES VMDPIDVKIS DAIMNMQDNS VQVSQKVFQG CGPPKPLPAG RISRSISESA
361  FSARFRPHHP EERPTTAAGT SLDRLVTDVK EKLKQAKKFW SSLPSNVCND ERMAAGNGNE
421  DDCWNGKGKS RYLFAVTGNG LANQGNNPEV QVDTSKPDIL ILRQIMALRV MTSKMKNAYN
481  GNDVDFFDIS DESSGEGSGS GCEYQQCPSE FDYNATDHAG KSANEKADSA GVRPGAQAYL
541  LTVFCILFLV MQREWR       (SEQ ID NO: 2)
```

Mature human Glypican-4 protein:

```
  1  AELKSKSCSE VRRLYVSKGF NKNDAPLHEI NGDHLKICPQ GSTCCSQEME EKYSLQSKDD
 61  FKSVVSEQCN HLQAVFASRY KKFDEFFKEL LENAEKSLND MFVKTYGHLY MQNSELFKDL
121  FVELKRYYVV GNVNLEEMLN DFWARLLERM FRLVNSQYHF TDEYLECVSK YTEQLKPFGD
181  VPRKLKLQVT RAFVAARTFA QGLAVAGDVV SKVSVVNPTA QCTHALLKMI YCSHCRGLVT
241  VKPCYNYCSN IMRGCLANQG DLDFEWNNFI DAMLMVAERL EGPFNIESVM DPIDVKISDA
301  IMNMQDNSVQ VSQKVFQGCG PPKPLPAGRI SRSISESAFS ARFRPHHPEE RPTTAAGTSL
361  DRLVTDVKEK LKQAKKFWSS LPSNVCNDER MAAGNGNEDD CWNGKGKSRY LFAVTGNGLA
421  NQGNNPEVQV DTSKPDILIL RQIMALRVMT SKMKNAYNGN DVDFFDISDE SSGEGSGSGC
481  EYQQCPSEFD YNATDHAGKS ANEKADSAGV RPGAQAYLLT VFCILFLVMQ REWR
541  (SEQ ID NO: 3)
```

FIGURE 6

Nucleotide sequence encoding the human glypican-4 precursor protein of SEQ ID NO: 2:

```
   1 gcctggcacc ggggaccgtt gcctgacgcg aggcccagct ctactttcg cccgcgtct
  61 cctccgcctg ctccgcctct ccaccaactc caactccttc tccctccagc tccactcgct
 121 agtccccgac tccgccagcc ctcggcccgc tgccgtagcg ccgcttccg tcggtccca
 181 aaggtgggaa cgcgtccgcc ccggcccgca ccatggcacg ccgcttg ccgcgcttc
 241 tctgcaccct ggcagtgctc agcgccgcgc tgctggctgc cgagctcaag tgaaaagtt
 301 gctcggaagt gcgacgtctt tacgtgtcca aaggcttcaa caagaacgat gcccctctcc
 361 acgagatcaa cggtgatcat cggtgaagatct gtcccaggg ttctacctgc tgctctcaag
 421 agatggagga gaagtacagc ctgcaaagta aagatgattt caaaagtgtg gtcagcgaac
 481 agtgcaatca tttgcaagct gtctttgctt cacgttacaa gaagtttgat gaattcttca
 541 aagaactact tgaaaatgca gagaaatccc tgaatgatat gtttgtgaag acatatgcc
 601 atttatacat gcaaaattct gagctattta aagatctctt cgtagagttg aaacgttact
 661 acgtggtggg aaatgtgaac ctggaagaaa tgctaaatga cttctggget cgcctcctgg
 721 agcgatgtt ccgcctggtg aactcccagt accactttac agatgagtat ctggaatgtg
 781 tgagcaagta tacggagcag ctgaagccct tggagatgt ccctcgcaaa ttgaagctcc
 841 aggttactcg tgcttttgta gcagcccgta ctttcgctca aggcttagcg gttgcgggag
 901 atgtcgtgag caaggtctcc gtggtaaacc ccacagccca gtgtacccat gccctgttga
 961 agatgatcta ctgctcccac tgccggggtc tgtgactgt gaagccatgt tacaactact
1021 gctcaaacat catgagaggc tgtttggcca accaagggga tctcgatttt gaatggaaca
1081 atttcataga tgctatgctg atggtggcag agaggctaga gggtccttc aacattgaat
1141 cggtcatgga tcccatcgat gtgaagattt ctgatgctat cccaagcc tatgaacatg caggataata
1201 gtgtttcaagt gtctcagaag gtttccagg gatgtggacc cccaagccc ctcccagctg
1261 gacgaatttc tcgttccatc tctgaaagtg ccttcagtgc tgcttcaga ccacatcacc
1321 ccgaggaacg cccaaccaca gcagctggca ctagttttgga ccgactggtt actgatgtca
1381 aggagaaact gaaacaggcc aagaaattct ggtcctccct tccgagcaac gtttgcaacg
1441 atgagaggat ggctgcagga aacggcaatg aggatgactg ttggaatggg aaaggcaaaa
```

FIGURE 6 (Continued)

```
1501  gcaggtacct  gtttgcagtg  acaggaaatg  gattagccaa  ccagggcaac  aacccagagg
1561  tccagttga   caccagcaaa  ccagacatac  tgatccttcg  tcaaatcatg  gctcttcgag
1621  tgatgaccag  caagatgaag  aatgcataca  atgggaacga  cgtggacttc  tttgatatca
1681  gtgatgaaag  tagtggagaa  ggaagtggaa  gtggctgtga  gtatcagcag  tgcccttcag
1741  agtttgacta  caatgccact  gaccatgctg  ggaagagtgc  caatgagaaa  gccgacagtg
1801  ctggtgtccg  tcctggggca  caggcctacc  tcctcactgt  cttctgcatc  ttgttcctgg
1861  ttatgcagag  agagtggaga  taattctcaa  actctgagaa  aaagtgttca  tcaaaaagtt
1921  aaaaggcacc  agttatcact  tttctaccat  cctagtgact  ttgcttttta  aatgaatgaa
1981  caacaatgta  cagtttttac  tatgtggcca  ctggtttaag  aagtgctgac  tttgttttct
2041  cattcagttt  tgggaggaaa  agggactgtg  cattgagttg  gttcctgctc  cccaaaacca
2101  tgttaaacgt  ggctaacagt  gtaggtacag  aactatagtt  agtgtgcat   ttgtgatttt
2161  atcactctat  tatttgtttg  tatgttttt   tctcatttcg  tttgtgggtt  tttttttcca
2221  actgtgatct  cgccttgttt  cttacaagca  aaccagggtc  ccttcttggc  agtaacatg
2281  tacgtatttc  tgaaatatta  aatagctgta  cagaagcagg  ttttatttat  catgttatct
2341  tattaaaaga  aaaagcccaa  aaagcagtaa  aatttccatt  tctccctgtt  attttagttg
2401  ccttatctgg  agagacgtgg  aggtgatttt  ctttttttta  aattattatt  aagacagaat
2461  gtgagggcac  aagcaggctt  ctgagcccact tgtcagattg  tattcaaagc  atcaatccaa
2521  gaaggaggtt  atgtgtactt  cattttattgg tgatagttgg  aagagactgc  agactactgc
2581  tttgaatgag  ttgaattaca  taagctaaga  tcactatagg  tccatttctt  gaacccactt
2641  atacataaaa  tgtaacccat  attctggata  atttctggata gttcacactt  tcatccccct  tgaaagatag
2701  aaagcattca  ggatgtccca  gttatcacat  gttcacactt  gggtttaggg  gtgttttttt
2761  ttaaaaccag  gcaggttagc  tagcccaccc  tgtgctagtt  ttcatgttca  cactgaccct
2821  atttgaatta  atatcctttg  ttagagtggt  cgagatttca  aacccaatta  tgtacaggga
2881  gctgtctgag  agctagccag  aactgggta   cagcctgggc  tcaggaata  gctgtcaaca
2941  ctcgggcaaa  gtttttgtct  gtgcatgtgt  atctccattt  gttttgggat  ccagttttt
3001  gttttaagag  agtataaggt  gtctcatttg  agtcttttc   ttacctagcc  ccctcttatc
3061  agtaaaacaa  aggacttgcc  atgttcaca   gcaatgtgct  acgatccaag  atatcagcca
3121  aggagcccac  ttaggggaga  actaggtgtc  cagatttttg  tatgtgttgt  ttttcttggg
3181  ggatggggtg  gggtgggagt  aggtagagct  gagaatacta  catcttagtg  gtgaccttta
```

FIGURE 6 (Continued)

```
3241 gccacgtggg tgaagtggca aaggccatgg ccatatctgt tgtcccaggc caaagactaa
3301 caactgcctt gggaatccct tcctttgtgtc cttaccaaat gatagctcat aaaactctga
3361 taatgtaaca aatcactttc aaaggagttc ccagaagtct tcagaaagac taaaattctg
3421 tctcttcctg ctttagacag ccattaagat cccaactaat tttaccgaac ctaaaaccca
3481 caaagaggtt gtttgtgtta ttgttcaatc ttcagttgta agagtaattc tctatttta
3541 tattgaaaca taattacttg atagctcagg gtctacatttt cattcaactt tttacaccaa
3601 atttctgcaga gtggtcaaaa tggaatattg ggggctgttg taaacagagg cttaatttta
3661 ttagaagtag ccagttattt attaaagcat gatgttaata aaataggcat attc
(SEQ ID NO: 1)
```

FIGURE 6 (Continued)

Figure 10
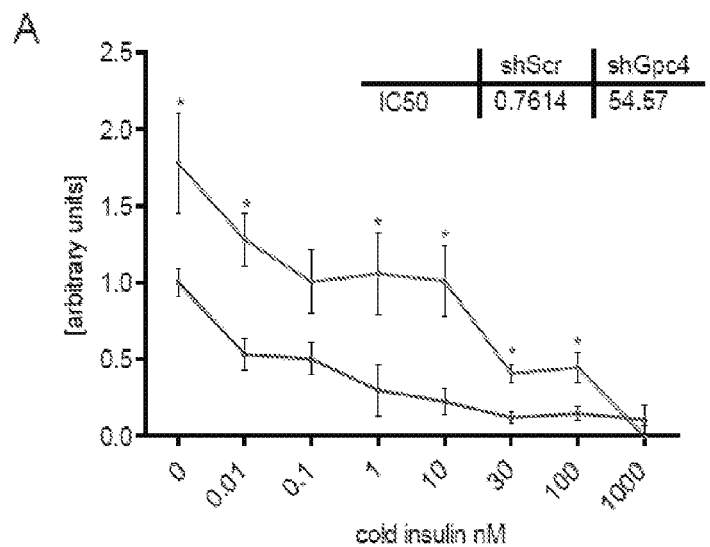
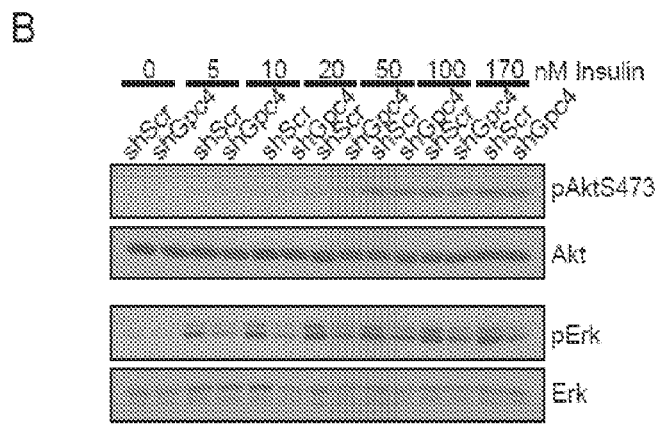
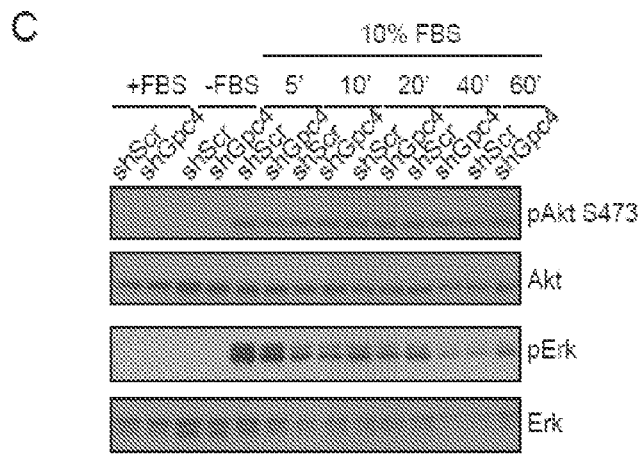

Figure 11
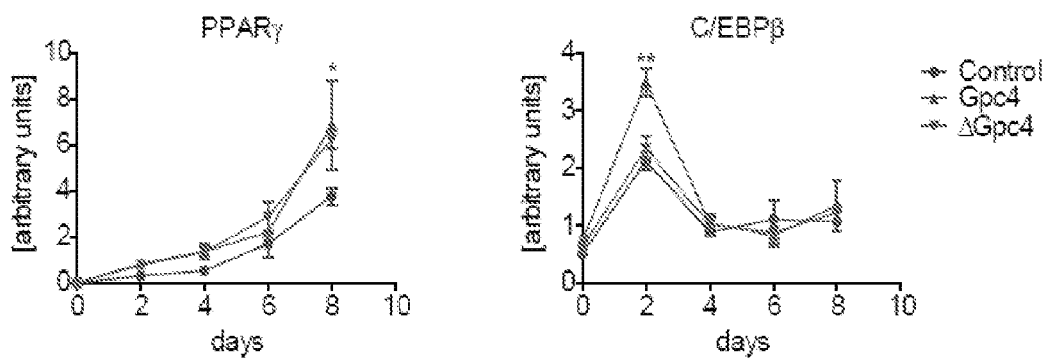
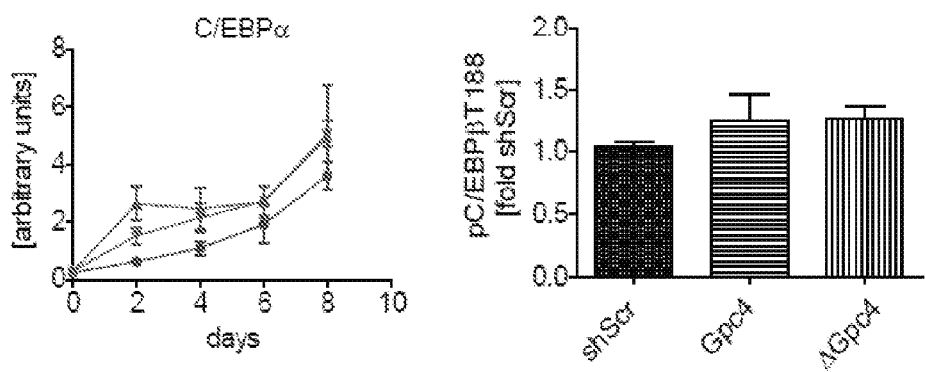
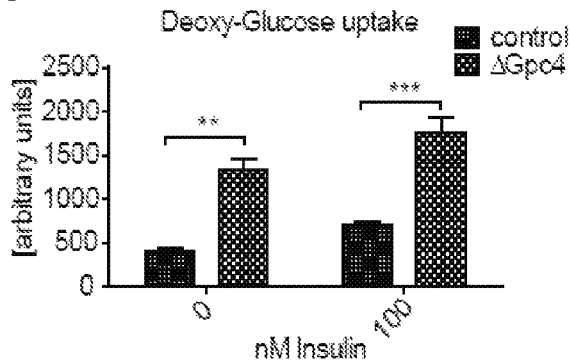

ID NO: 9]. Actin was used as loading
GLYPICAN-4 BASED COMPOSITIONS AND METHODS FOR TREATING AND DIAGNOSING INSULIN RESISTANCE

GOVERNMENT SUPPORT

This invention was made with government support under grant Nos. DK031036, DK082659 and DK036836 awarded by the National Institutes of Health. The government has certain rights in the invention.

REFERENCE TO SEQUENCE LISTING, TABLE, OR COMPUTER PROGRAM LISTING

The instant application contains a Sequence Listing which has been submitted in ASCII format via EFS-Web and is hereby incorporated by reference in its entirety. Said ASCII copy, created on Nov. 2, 2015, is named JDP-155US02 SL.txt and is 25,558 bytes in size.

BACKGROUND

Obesity is the main cause of insulin resistance in humans, and, in many individuals, the first step in the development of type 2 diabetes and metabolic syndrome. The adverse metabolic effects of increasing fat mass depend heavily on its anatomical distribution, with visceral white adipose tissue (WAT) driving the development of insulin resistance and associated metabolic diseases (1). In contrast increased subcutaneous WAT is not associated with insulin resistance and, in some circumstances, has even been shown to have protective effects (2, 1).

Expansion of adipose tissue is achieved by increased lipid storage in existing adipocytes and de novo differentiation of preadipocytes. Various autocrine, paracrine and endocrine factors control adipocyte differentiation (3). Among them insulin is important in regulation of differentiation and lipid accumulation in vitro and in vivo (4). White adipose tissue is also an important endocrine organ, secreting various cytokines and hormones (adipokines) regulating whole body metabolism and insulin sensitivity (5, 6, 7).

It was previously identified that a set of developmentally-regulated genes that are differentially expressed in subcutaneous and visceral adipose tissue of mice and men (8). Among these, the patterning gene glypican-4 (Gpc4) is not only differentially expressed in these depots, but its expression in human WAT is also highly correlated with body mass index (BMI) and adipose distribution as measured by waist-to-hip ratio (WHR). Gpc4 belongs to a six member family of glycosylphosphatidylinositol (GPI) anchored heparan sulfate proteoglycans. Lacking transmembrane and intracellular domains, glypicans function as co-receptors for a variety of growth factors including Wnt, BMPs, FGF and Hedgehog (9, 10, 11). Little is known about the signaling functions of Gpc4. Mammalian Gpc4 has been reported to bind to FGF2 via its heparan sulfate chains in neuronal cells and to function as a low affinity receptor for endostatin (12, 13). The role of Gpc4 in adipocytes and its relationship to metabolic regulation remains unknown.

SUMMARY

Embodiments of this invention are based on our novel and non-obvious showings that Gpc4 is important for adipocyte differentiation by interacting with and regulating insulin receptor activation and its downstream signaling. This interaction is preserved in a soluble non-membrane anchored mutant of Gpc4. Furthermore, provided herein is evidence that Gpc4 is released from adipose tissue, and that serum Gpc4 is a marker for BMI and insulin sensitivity in mice and human. Thus, Gpc4 can serve as a novel adipokine being released from adipose tissue with the ability to enhance insulin sensitivity.

BRIEF DESCRIPTION OF THE FIGURES

FIG. 6 Amino acid sequences of human glypican-4 precursor [SEQ ID NO: 2] and mature proteins [SEQ ID NO: 3] as well as the nucleotide sequence of human glypican-4 precursor protein [SEQ ID NO: 1].

FIG. 10 shows (A) Insulin binding to confluent shScr and shGpc4 preadipocytes. 125I-insulin was competed with increasing concentrations of unlabeled insulin. Values were background subtracted and normalized to protein concentration. (n=6). (B) Western Blot for pAktS473, pErk and the respective unphosphorylated proteins of shScr and shGpc4 cells stimulated with the indicated concentrations of insulin for 20 minutes. (C) Western Blot for pAktS473, pErk and the respective unphosphorylated proteins of shScr and shGpc4 cells stimulated with 10% FBS after 3 hours serum withdrawal.

FIG. 11 shows (A) Realtime PCR for Pparγ, C/EBPα and C/EBPβ during an eight day time course of differentiation of control Gpc4 and ΔGpc4 overexpressing cells. * indicates significantly higher expression in ΔGpc4 and Gpc4 vs. control cells (n=5). (B) Quantification of phospho-C/EBPβ hr188 normalized to total C/EBPβ of control Gpc4 and ΔGpc4 overexpressing cells 24 h after induction (n=3). (C) 14C-Deoxy-glucose uptake was measured in serum starved 3T3-LI control or ΔGpc4 overexpressing adipocytes exposed for 45 minutes to 0 or 100 nM insulin (n=3).

DETAILED DESCRIPTION

Figure 1:
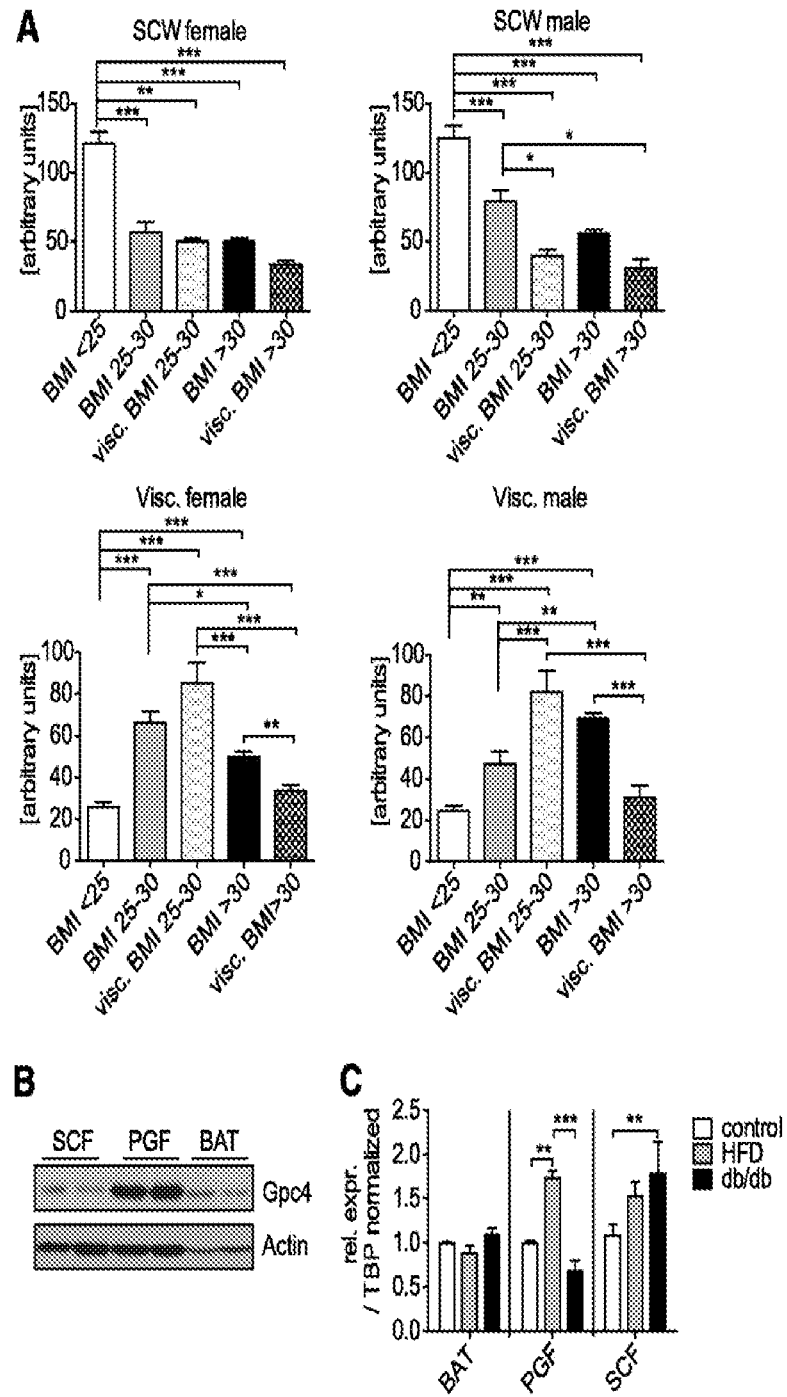
FIG. 1 shows Gpc4 is differentially regulated in subcutaneous and visceral WAT upon weight gain. A: Gpc4 expression in subcutaneous (SCW) and visceral (Visc.) fat of 77 female and 83 male nondiabetic subjects, ranging from lean to obese, grouped by BMI. Visc. BMI 25-30 and visc. BMI >30 indicates subjects with a CT or MRI ratio between subcutaneous and visceral fat areas >0.4 in the given BMI range. B: Western blot for Gpc4 from 6-week-old C57BL/6 male mice. Actin is used as loading control. C: qPCR for Gpc4 from the indicated fat depots of C57BL/6 mice fed an HFD for 8 weeks, db/db and control mice. Control mice are C57BL/6 chow diet-fed mice and db/+ mice combined (HFD, n=4; db/db, n=6; controls, n=4-6). BAT, brown adipose tissue; PGF, perigonadal fat; SCF, subcutaneous flank fat. *P<0.05; P<0.01; *P<0.001.

Provided herein are methods for increasing insulin sensitivity in a subject. A method may comprise administering to a subject in need of increased insulin sensitivity a therapeutically effective amount of a glypican-4 agent. Also provided herein are methods for determining whether a subject is or is likely to become insulin resistant. A method may comprise determining the level of glypican-4 in a subject, wherein an elevated level of glypican-4 indicates that a subject is or is likely to become insulin resistant.

The invention is based at least on the discovery that circulating glypican-4 levels correlate with body mass index and insulin sensitivity in humans, and that glypican-4 interacts with the insulin receptor and enhances insulin receptor signaling and enhances adipocyte differentiation.

Glypican-4 is also known as RP6-198C21.1, K-glypican and has Gene ID:2239. The human glypican-4 precursor protein consists of 556 amino acids, of which amino acids 1-22 correspond to the signal peptide. The amino acid sequence of the precursor protein is provided as GenBank Accession No. NP_001439 and is set forth herein as SEQ ID NO: 2 (FIG. 6). The amino acid sequence of the mature protein, corresponding to amino acids 23-556 of SEQ ID NO: 2 is set forth as SEQ ID NO: 3 (FIG. 6). The nucleotide sequence encoding the human glypican-4 precursor protein is provided as GenBank Accession No. 1.NM_001448.2 and is set forth herein as SEQ ID NO: 1.

In certain embodiments, a method comprises administering to a subject a glypican-4 agent. An "agent" can be any type of molecule, including a peptide, polypeptide, protein, nucleic acid (e.g., RNA or DNA) or other type of molecule that mimics glypican-4 or induces a biological response that is induced by a wild type or naturally occurring glypican-4. In preferred embodiments, a glypican-4 agent is a protein that binds to (or interacts with) the insulin receptor when insulin is not bound to the receptor. In certain embodiments, a glypican-4 agent is a protein comprising all or a portion of SEQ ID NO: 2 or 3, or a protein comprising an amino acid sequence that is at least 70%, 80%, 90%, 95%, 97%, 98%, or 99% identical to SEQ ID NO: 2 or 3. Amino acid differences may be amino acid substitutions, e.g., a conservative amino acid substitution, amino acid deletions or additions. In certain embodiments, a glypican-4 agent is a protein comprising an amino acid sequence that differs from an amino acid sequence of the naturally occurring human glypican-4, e.g., having SEQ ID NO: 2 or 3, and comprising at most 100, 80, 50, 30, 25, 20, 15, 10, 9, 8, 7, 6, 5, 4, 3, 2, 1 amino acid differences, e.g., amino acid substitutions, deletions or additions.

In certain embodiments, a glypican-4 agent comprises, consists or consists essentially of, a fragment of glypican-4 and comprising, e.g., up to 10, 15, 20, 30, 40, 50, 75, 100, 150, 200, 250, 300, 350, 400, 450 or 500 consecutive amino acids of a full length glypican-4 protein, e.g., a human glypican-4 protein having SEQ ID NO: 2 or 3. In certain embodiments, a glypican-4 agent is a protein that is at least 70%, 80%, 90%, 95%, 97%, 98%, or 99% identical to a fragment of a wild type or naturally occurring glypican-4, e.g., a human glypican-4 consisting of SEQ ID NO: 2 or 3.

A glypican-4 agent may also be a fusion protein comprising, e.g., a glypipcan-4 protein or fragment or analog thereof, that is covalently linked to an unrelated protein or peptide to, e.g., stabilize the glypican-4 protein or fragment or analog thereof, facilitate transport to the proper target tissue (e.g., adipose tissue) or increase its solubility. In one embodiment, a glypican-4 protein or portion or analog thereof (e.g., a protein that is similar to a naturally occurring glypican-4 protein, e.g., a protein having SEQ ID NO: 2 or 3) is fused to an immunoglobulin constant region, e.g., an IgG constant region, which may comprise the hinge, CH2 and/or CH3 domains.

In certain embodiments, a glypican-4 agent comprises a GPI-anchor, such as the naturally-occurring GPI anchor that is present on a naturally occurring glypican-4. A glypican-4 agent may also be an agent that does not comprise a GPI-anchor, such as a protein in which it was specifically deleted or its site of attachment was mutated so as to prevent its attachment to a GPI-anchor. A glypican-4 agent that is deprived of a GPI-anchor is a soluble glypican-4 protein or analog thereof. As shown herein, soluble glypican-4 agents also bind to the insulin receptor and increase insulin sensitivity.

In certain embodiments, a nucleic acid encoding a glypican-4 agent is administered to a subject. A nucleic acid may comprise the coding sequence of a glypican-4 protein or analog thereof operably linked to a promoter and optionally an enhancer and any other elements necessary for expressing the glypican-4 protein or analog from the nucleic acid. A nucleic acid may be a vector, such as an expression vector, e.g., viral vector. The nucleic acid may express the glypican-4 protein or analog in a tissue specific manner, e.g., specifically in adipose tissue, such as white adipose tissue.

Methods of Treatment

Provided herein are methods for treating a subject comprising administering to the subject a glypican-4 agent to increase the subject's sensitivity to insulin. A method may comprise administering to a subject in need thereof a therapeutically effective amount of a glypican-4 agent, e.g., to increase insulin sensitivity of the subject.

The term "effective amount" as used herein means an amount effective, at dosages and for periods of time necessary to achieve the desired result, for example, to treat the specific disorder.

The term "treating" refers to an approach for obtaining beneficial or desired results, including clinical results. Beneficial or desired clinical results can include, but are not limited to, alleviation or amelioration of one or more symptoms or conditions, diminishment of extent of disease, stabilization of the state of disease, prevention of spread or development of the disease or condition (e.g., insulin resistance), delay or slowing of disease progression, amelioration or palliation of the disease state, and remission (whether partial or total). "Treating" can also mean prolonging survival of a patient beyond that expected in the absence of treatment. "Treating" can also mean inhibiting the progression of disease, slowing the progression of disease temporarily, although more preferably, it involves halting the progression of the disease permanently. A method may increase insulin sensitivity by at least 10%, 20%, 30%, 40%, 50%, 60%, 70%, 80%, 90%, 100% (2 fold), 3 fold, 5 fold or more. A method may reduce insulin resistance by at least 10%, 20%, 30%, 40%, 50%, 60%, 70%, 80%, 90%, 100% (2 fold), 3 fold, 5 fold or more. Insulin sensitivity or resistance may be measured by methods known in the art, e.g., as further described herein.

A subject who may be treated by administration of a glypican-4 agent may be a subject in need of increased insulin sensitivity, e.g., an insulin resistant subject or a subject who is likely to become insulin resistant. For example, a subject in need of increased insulin sensitivity may be a subject who is overweight or obese, and has, e.g., a BMI ≥25 or 30. A subject in need of a glypican-4 agent may also be a subject having the metabolic syndrome, type 1 diabetes, type 2 diabetes or a subject having hyperlipidemia or hyperglycemia. A subject may be a mammal, such as a human.

A method may comprise first identifying a subject as being in need of glypican-4, such as a subject who is in need of an agent for increasing insulin sensitivity, and if a subject has been identified as such, then administering to the subject a glypican-4 agent. A method may comprise determining whether a subject (i) is insulin resistant or likely to become insulin resistant; (ii) has metabolic syndrome (syndrome X); (iii) has type 2 diabetes; (iv) had type 1 diabetes; (v) is obese; (vi) is overweight; (vii) has hyperglycemia; (viii) has hyperlipidemia; or (ix) has any pre-insulin resistance characteristics; and if the subject has any one or more of these conditions, then administering to the subject a glypican-4 agent.

A method may also first comprise determining whether the subject would be responsive to a glypican-4 therapy, e.g., as further described below, and if the subject is determined to be a likely responder to a glypican-4 agent therapy, then administering to the subject a glypican-4 agent.

Administration of a glypican-4 agent to a subject may be systemic or local. Local administration may include administration into a tissue having cells that have insulin receptors, e.g., adipose tissue, such as white adipose tissue.

Also provided herein are methods for stimulating the differentiation of a preadipocyte. A method may comprise contacting a pre-adipocyte with a glypican-4 agent to stimulate its differentiation. A pre-adipocyte may be an isolated cell or in a cell population. A pre-adipocyte may be obtained from a subject or be a cell line. In one embodiment, a pre-adipocyte (or a population of pre-adipocytes) is obtained from a subject and contacted ex vivo with a glypican-4 agent to stimulate their differentiation into adipocytes.

Therapeutic Administration and Pharmaceutical Compositions

A therapeutic (e.g., a glypican-4 agent) may be administered to a patient using standard techniques known in the art. The therapeutic may be administered systemically, or may be administered directly at the site at which a target cell is located, e.g., white adipose tissue. Delivery to the site includes topical administration, injection to the site, or surgical implantation, for example in white adipose tissue. A treatment may comprise one or more doses, which may be daily, weekly, monthly or according to another regimen, as determined by a physician.

The concentration and amount of the therapeutic to be administered will vary, depending on the disorder to be treated, the type of therapeutic that is administered, the mode of administration, and the age and health of the patient. However, a person of skill in the art will be able to determine the proper amount.

To aid in administration, the therapeutic may be formulated as an ingredient in a pharmaceutical composition. Therefore, in a further embodiment, there is provided a pharmaceutical composition comprising a therapeutic, and a pharmaceutically acceptable diluent. Therefore, also provided herein are pharmaceutical compositions for use in treating a disorder, such insulin resistance. The compositions may routinely contain pharmaceutically acceptable concentrations of salt, buffering agents, preservatives and various compatible carriers. For all forms of delivery, the therapeutic may be formulated in a physiological salt solution. Therapeutics may be incorporated in a liposome or other biomaterial useful for protecting and/or preserving the therapeutic until it is delivered to the target cell. A liposome may also help target a therapeutic to a desired location, e.g., white adipose tissue or skeletal tissue.

A pharmaceutical composition may additionally contain other therapeutic agents useful for treating a disorder, such as other agents for treating obesity, insulin resistance, glucose intolerance, hyperlipidemia, Syndrome X or Type II diabetes. For example, a composition may comprise a glypican-4 agent and a second therapeutic for treating obesity, insulin resistance, glucose intolerance, hyperlipidemia, Syndrome X or Type II diabetes, e.g., a PPAR-$\gamma$ agonist, such as a thiazolidinedione. Exemplary thiaxolidinediones include Rosiglitazone (AVANDIA), Pioglitazone (Actos), Troglitazone (Rezulin), Rivoglitazone (MCC-555) and Ciglitazone. Combinations may be present in a single pharmaceutical compositions, or in different pharmaceutical compositions, which are administered simultaneously or sequentially to a subject.

For example, a subject receiving a glypican-4 agent may also receive one or more of the following drugs for treating obesity:

Catecholamines and their derivatives, such as phentermine (e.g., ADIPEX-P) and other amphetamine based drugs; metamphetamine-based drugs (e.g., DESOXYN and DESOXYN GRADUMET) and benzphetamine based drugs (e.g., DIDREX); phendimetrazine (e.g., ADIPOST; APPECON; BONTRIL PDM; BONTRIL SLOW RELEASE; MELFIAT); phentermine (LO-NAMIN; OBENIX; OBEZINE; OBY-CAP; PHENDIET; PLEGINE; PRELU-2; PRELU-2 TR; PRO-FAST SA; STATOBEX; T-DIET; TERAMINE; ZANTRLY);

anti-depressants and mood stabilizers, such as bupropion; topiramate; diethylpropion (e.g., TENUATE; TENUATE DOSPAN; TEPANIL);

drugs blocking the cannabinoid receptors;

drugs that increase of the body's metabolism;

drugs that interference with the body's ability to absorb specific nutrients in food (such as Orlistat (XENICAL; ALLI); glucomannan and guar gum;

Anorectics (such as DEXEDRINE and digoxin); and

Others: ZGN-433; GT 389-255 (being developed by Peptimmune, Inc.).

A subject receiving a glypican-4 inhibitor may also receive one or more of the following drugs for treating Type II diabetes:

Insulin sensitizers, such as Biguanides, e.g., Metformin (GLUCOPHAGE); Thiazolidinediones (TZDs), also known as "glitazones," that bind to PPAR$\gamma$ and include rosiglitazone (AVANDIA; AVANDARYL; AVENDAMET), pioglitazone (Actos), troglitazone (Rezulin; withdrawn) and Darglitazone;

Secretagogues, such as Sulfonylureas, e.g., tolbutamide (ORINASE; Tol-Tab); acetohexamide (DYMELOR); tolazamide (TOLINASE); chlorpropamide (DIABINESE); glipizide (GLUCOTROL; GLUCOTROL XL; GLIPIZIDE XL; METAGLIP); glyburide (DIABETA, MICRONASE, GLYNASE); glimepiride (AMARYL; DUETACT); gliclazide (DIAMICRON); DIABETA; DIABINESE; GLYCRON; GLYNASE; and GLYNASE PRES TAB;

Nonsulfonylurea secretagogues, such as Meglitinides, e.g., repaglinide (PRANDIN); nateglinide (STARLIX); FORAMET; GLUMETZA; PRANDIMET; and RIOMET;

Alpha-glucosidase inhibitors, e.g., miglitol (GLYSET); and acarbose (PRECOSE/GLUCOBAY; PRECOSE);

Peptide analogs, such as Incretin mimetics, e.g., glucagon-like peptide-1 (GLP-1); gastric inhibitory peptide (glucose-dependent insulinotropic peptide, GIP), such as Exenatide (also Exendin-4, marketed as BYETTA); Liraglutide (VICTOZA); and Taspoglutide;

Gastric inhibitory peptide analogs;

Small molecule analogs, such as Dipeptidyl peptidase-4 (DPP-4) inhibitors, e.g., vildagliptin (GALVUS); sitagliptin (JANUVIA; JANUMET); saxagliptin (ONGLYZA; KOMBIGLYZE XR); linagliptin (TRADJENTA); and Alogliptin;

Amylin analogues, such as pramlintide (SYMLIN; SYMLIN PEN; SYMLIN PEN 120; SYMLINPEN 60); and Others: APD597 (Arena Pharmaceuticals); salsalate; and salsalte analogues and derivatives; WELCHOL; Cr-GTF; CRM; CYCLOSET; ACTOPLUS MET; ACTOPLUS MET XR; GLUCOVANCE.

A subject receiving a glypican-4 may also receive one or more of the following drugs for insulin resistance: glucosamine, rifampicin, isoniazid, olanzapine, risperidone, progestogens, corticosteroids, glucocorticoids, methadone, many antiretrovirals, metformin, a thiazolidinedione, and Exenatide (BYETTA).

A preferred embodiment of the present invention is the administration of a pharmaceutically acceptable formulation of a glypican-4 agent. A "pharmaceutically acceptable formulation" is one that is suitable for administering a glypican-4 in a manner that gives the desired results and does not also produce adverse side effects sufficient to convince a physician that the potential harm to a patient is greater than the potential benefit to that patient.

A pharmaceutical composition may be prepared by known methods for the preparation of pharmaceutically acceptable compositions suitable for administration to patients, such that an effective quantity of the therapeutic and any additional active substance or substances, is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the pharmaceutical compositions include, albeit not exclusively, solutions of the therapeutic in association with one or more pharmaceutically acceptable vehicles or diluents, and contained in buffer solutions with a suitable pH and iso-osmotic with physiological fluids.

The proportion and identity of a pharmaceutically acceptable diluent used with a therapeutic is determined by the chosen route of administration, compatibility with live cells, and standard pharmaceutical practice. Generally, a pharmaceutical composition will be formulated with components that will not kill or significantly impair the biological properties of the therapeutic.

A pharmaceutical composition may be administered to a patient in a variety of forms depending on the selected route of administration, as will be understood by those skilled in the art. For example, a composition may be administered topically, surgically or by injection to the desired site. In certain embodiments, a therapeutic is administered topically or by injection (subcutaneously, intravenously, intramuscularly, etc.) directly at the desired site where the target cells, e.g., white adipose cells, are located in the patient.

Administration of a glypican-4 may also be combined with a weight reducing diet and/or exercise.

Diagnostic and Prognostic Methods

Also provided herein are methods for determining the level of insulin sensitivity or resistance of a subject or whether a subject is or is likely to become insulin resistant. A method may comprise providing a sample from a subject and determining the level of glypican-4 in the sample, wherein a level of glypican-4 that is higher than the level of glypican-4 in a subject who is not insulin resistant indicates that the subject is or is likely to become insulin resistant, whereas a level of glypican-4 that is similar to or lower than that in a subject who is not insulin resistant indicates that a subject is not insulin resistant and is not likely to become insulin resistant. A method may further first comprise obtaining a sample from a subject.

A method may comprise obtaining a sample from a subject, e.g., a sample of tissue or biological fluid. A sample of tissue may be a sample of a tissue comprising cells having an insulin receptor. A sample of tissue may be, e.g., adipose tissue, such as white adipose tissue, or muscle tissue. A sample of biological fluid may be a sample of blood, serum, urine or tears.

In one embodiment, a method may comprise determining the level of glypican-4 in the serum of a subject (e.g., in a sample of serum from the subject), wherein a level of glypican-4 that is ≥7 ng/ml, 9 ng/ml or 10 ng/ml (preferably ≥9 ng/ml) indicates that the subject is insulin resistant or likely to become insulin resistant. In one embodiment, the subject is not obese or overweight. As described herein, non obese subjects (BMI <30) with high serum glypican-4 (≥9 ng/ml) levels showed the same degree of insulin resistance as measured by euglycemic clamp, fasting plasma insulin and HOMA-IR as obese subjects, independent of serum glypican-4 levels. Thus, in one embodiment, a method for determining whether a non-obese subject (BMI <30) is insulin resistant or likely to become insulin resistant, comprises:

(i) providing a sample of serum from the subject; and
(ii) determining the level of glypican-4 in the serum of the subject, wherein a level of glypican-4 in the serum sample that is higher than a control value (e.g., a statistically significant level of glypican-4 in subjects who are not insulin resistant), indicates that the subject is or is likely to become insulin resistant; whereas a level of glypican-4 in the serum sample that is similar to or lower than the control value indicates that the subject is not or is not likely to become insulin resistant. A control value may be, e.g., 4 ng/ml, 5 ng/ml, or 6 ng/ml.

Also provided herein are methods for determining whether a subject is responding to a treatment for insulin resistance or for increasing insulin sensitivity. A method may comprise providing a sample of a subject that is being treated for insulin resistance and determining the level of glypican-4 in the sample; wherein a higher level of glypican-4 in the sample relative to that at an earlier time during the treatment or prior to the treatment indicates that the subject is not responding to the treatment, whereas a lower level of glypican-4 in the sample relative to that at an earlier time during the treatment or prior to the treatment indicates that the subject is responding to the treatment. A sample may be a serum sample.

Further provided are methods for determining whether a subject is likely to respond to a treatment for insulin resistance or for increasing insulin sensitivity. A method may comprise providing a sample of a subject that has received a dose (e.g., a single dose) of a drug for treating insulin resistance or increasing insulin sensitivity, and determining the level of glypican-4 in the sample; wherein a higher level of glypican-4 in the sample relative to that prior to the administration of the drug indicates that the subject is not likely to respond to the drug, whereas a lower level of glypican-4 in the sample relative to that prior to the administration of the drug indicates that the subject is likely to respond to the drug. A sample may be a serum sample. A drug for insulin resistance may be a glypican-4 agent. If the drug is a glypican-4 agent, then the method specifically measures the naturally-occurring glypican-4 for determining the likelihood of response of the subject to a glypican-4 treatment. A drug may also be PPAR-γ agonist, such as a thiazolidinedione. Exemplary thiaxolidinediones include Rosiglitazone (AVANDIA), Pioglitazone (Actos), Troglitazone (Rezulin), Rivoglitazone (MCC-555), Ciglitazone. The assays described herein may also be used to determine the response of a subject to any of the following insulin resistance therapeutics:

glucosamine, rifampicin, isoniazid, olanzapine, risperidone, progestogens, corticosteroids, glucocorticoids, methadone, many antiretrovirals, metformin,a thiazolidinedione, and Exenatide (Byetta).

If a subject is determined as a likely responder to a therapeutic (drug) for increasing insulin sensitivity or reducing or preventing insulin resistance, then a method may comprise administering to the subject the therapeutic for increasing insulin sensitivity or reducing or preventing insulin resistance.

Instead of determining the level of glypican-4, a method may comprise determining the level of signal transduction that is induced by the action of glypican-4 on its target, e.g., the insulin receptor. For example, a method may comprise measuring the level of transactivation of C/EBPα and/or PPARγ.

Also provided herein are compositions for diagnostic/prognostic and biomarker applications. A composition may comprise a reagent for determining the level of glypican-4 in a sample. A reagent may be any molecule or complex of molecules that can bind to glypican-4, such as an antibody or antigen binding fragment thereof or a portion of an insulin receptor to which glypican-4 binds. A composition may also comprise one or more reagents necessary for detecting and/or measuring activation of the signal transduction pathway that is induced by glypican-4, e.g., in adipose cells.

Also provided are kits for diagnostic/prognostic and biomarker applications. A kit may comprise a reagent for detecting glypican-4 and one or more other compositions or elements that may be necessary for measuring glypican-4 levels in a sample. Kits may also comprise reagents necessary for detecting and/or measuring activation of the signal transduction pathway that is induced by glypican-4, e.g., in adipose cells.

Assays for Identifying Therapeutics for Treating Insulin Resistance

Further provided herein are assays that may be used to identify agents for increasing insulin sensitivity or for treating insulin resistance. An assay may comprise identifying an agent that binds to the insulin receptor or IGF1R in a similar manner as glypican-4 binds to the insulin receptor or IGF1R. A method may comprise contacting an insulin receptor or IGF1R or fragment or analog thereof that binds to glypican-4 with a test compound and determining whether the test compound binds to the insulin receptor or IGF1R or fragment or analog thereof, wherein a test compound that binds to the insulin receptor or IG1R or fragment or analog thereof indicates that the test compound is a compound that may be used for increasing insulin sensitivity. The assay may be following by additional assays that are used for determining the effect of a drug on insulin resistance.

Also provided are isolated complexes comprising, e.g., a glypican-4 protein or fragment or analog thereof and an insulin receptor or IGF1R fragment or analog thereof. Compositions comprising these isolated complexes are also encompassed herein. Compositions may further comprise additional ingredients, e.g., a test compound.

In certain embodiments, a method may comprise contacting an insulin receptor or portion or analog thereof with glypican-4 or fragment or analog thereof that binds to the insulin receptor in the presence of a test compound and determining whether the test compound affects the binding of the insulin receptor or fragment or analog thereof with glypican-4 or fragment or analog thereof. A compound that increases the binding of the insulin receptor and glypican-4 is a compound that may increase insulin sensitivity.

In some embodiments, the test compounds are initially members of a library, e.g., an inorganic or organic chemical library, peptide library, oligonucleotide library, or mixed-molecule library. In some embodiments, the methods include screening small molecules, e.g., natural products or members of a combinatorial chemistry library.

A given library can comprise a set of structurally related or unrelated test compounds. Preferably, a set of diverse molecules should be used to cover a variety of functions such as charge, aromaticity, hydrogen bonding, flexibility, size, length of side chain, hydrophobicity, and rigidity.

Combinatorial techniques suitable for creating libraries are known in the art, e.g., methods for synthesizing libraries of small molecules, e.g., as exemplified by Obrecht and Villalgordo, Solid-Supported Combinatorial and Parallel Synthesis of Small-Molecular-Weight Compound Libraries, Pergamon-Elsevier Science Limited (1998). Such methods include the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of libraries, including small molecule libraries, are commercially available.

In some embodiments, the test compounds are peptide or peptidomimetic molecules, e.g., peptide analogs including peptides comprising non-naturally occurring amino acids or having non-peptide linkages; peptidomimetics (e.g., peptoid oligomers, e.g., peptoid amide or ester analogues, .beta.-peptides, D-peptides, L-peptides, oligourea or oligocarbamate); small peptides (e.g., pentapeptides, hexapeptides, heptapeptides, octapeptides, nonapeptides, decapeptides, or larger, e.g., 20-mers or more); cyclic peptides; other non-natural or unnatural peptide-like structures; and inorganic molecules (e.g., heterocyclic ring molecules). In some embodiments, the test compounds are nucleic acids, e.g., DNA or RNA oligonucleotides.

In some embodiments, test compounds and libraries thereof can be obtained by systematically altering the structure of a first test compound. Taking a small molecule as an example, e.g., a first small molecule is selected that is, e.g., structurally similar to glypican-4. For example, in one embodiment, a general library of small molecules is screened, e.g., using the methods described herein, to select a first test small molecule. Using methods known in the art, the structure of that small molecule is identified if necessary and correlated to a resulting biological activity, e.g., by a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds.

In some embodiments, test compounds identified as "hits" in a first screen are selected and optimized by being systematically altered, e.g., using rational design, to optimize binding affinity, avidity, specificity, or other parameter. Such potentially optimized structures can also be screened using the methods described herein. Thus, in one embodiment, the invention includes screening a first library of test compounds using a method described herein, identifying one or more hits in that library, subjecting those hits to systematic structural alteration to create one or more second generation compounds structurally related to the hit, and screening the second generation compound. Additional rounds of optimization can be used to identify a test compound with a desirable therapeutic profile.

Test compounds identified as hits can be considered candidate therapeutic compounds, useful in the methods of treating and preventing disorders described herein. Thus, the invention also includes compounds identified as "hits" by a method described herein, and methods for their administration and use in the treatment, prevention, or delay of development or progression of a disease described herein. The following examples should not be construed as limiting the scope of this disclosure.

Exemplification
Materials and Methods
Human Subjects

Paired samples of visceral and subcutaneous adipose tissue were obtained from 160 subjects as previously described and as known by one of ordinary skill in the art (8). All subjects gave written informed consent before taking part in the study.

Mice

All protocols were approved by the Institutional Animal Care and Use Committee of the Joslin Diabetes Center and in accordance with NIH guidelines. Mice (Jackson Lab; Bar Harbor, Me.) were maintained on a 12 h-light/dark cycle and fed a chow diet (9F5020; PharmaServ; Framingham, Mass.) or high fat diet (OpenSource Diet D12492, Research Diet; New Brunswick, N.J.).

Constructs

Gpc4 cDNA clones were obtained from Open Biosystems (Waltham, Mass.). An HA-tag was inserted after the signal peptide for native Gpc4 and the cDNA was cloned into the pCDH-puro lentiviral vector (Systems Biosciences; Mountain View, Calif.). Gpc4Δ529SAG531::HHHHHH (ΔGpc4) [SEQ ID NO: 11] was created by site directed mutagenesis (Stratagene) using the primers fwd:CGAGAAAGCTGAC-CACCATCACCATCACCATGGTGCCCATGCAG [SEQ ID NO: 4] rev:CTGCATGGGCACCATGGTGATGGT-GATGGTGGTCAGCTTTCTCG [SEQ ID NO: 5]. A 6xHis tag was inserted at the N-terminus after the signal peptide and cloned into the pCDH-puro vector. All constructs were sequence verified. shRNA lentiviral vectors (pLKO.1) were obtained from Open Biosystems. shGpc4 shRNA was targeted against the sequence GCCACTGGTTTAAGCAAT-GTT [SEQ ID NO: 6]. A scrambled shRNA (shScr) targeting the sequence AGGTTAAGTCGCCCTCG [SEQ ID NO: 7] served as control.

Oligonucleotide Pull-Down Assays

Pull downs were performed as previously described and as known by one of ordinary skill in the art (29).

Cell Culture

3T3-L1 cells were cultured in DMEM 4.5 g/l glucose, 10% FBS and 2.5 g/ml puromycin. Differentiation was induced with 170 nM insulin, 500 μM IBMX, 400 ng/ml dexamethasone with or without 1 μM troglitazone (TZD). Oil Red O staining was performed as previously described and as known by one of ordinary skill in the art (33). Lentiviruses were produced in 293FT cells using the packaging plasmids psPAX2 and pMD2.G.

Quantitative Real Time PCR (qPCR)

cDNA synthesis and qPCR were performed as previously described and as known by one of ordinary skill in the art (1). Relative expression levels were calculated by the ΔΔCt method using TBP as reference. The primers used are described in (8,29).

Western Blots

Cells were lysed in 150 mM NaCl, 50 mM Tris-HCl (pH7.4), 1 mM EDTA, 1% Triton X-100 with protease and phosphatase inhibitors (Sigma; St. Louis, Mo.). The following antibodies were used: HRP-Actin (SantaCruz; Santa Cruz, Calif.), pTyrosine (4G10), pIRS-1Y896 (Biosource; Grand Island, N.Y.) pIRSY612 (Invitrogen; Grand Island, N.Y.), IRS-1 (BD), pC/EBPβThr188, C/EBPα, C/EBPβ, pAktS473, Akt, pERK, Erk, IRβ (all Cell Signaling; Danvers, Mass.). The Gpc4 antibody was raised against the peptide: EVRRLYVSKGFNKNDAPLYE (aa 32-52) [SEQ ID NO: 8] in rabbits and affinity purified against the peptide.

Immunoprecipitations

Protein lysates were incubated with mouse insulin receptor antibody (Cell-Signaling; Danvers, Mass.) overnight. Co-Immunoprecipitation was performed using magnetic protein-A micro beads and μColumns (Miltenyi; Cambridge, Mass.). For the quantification of insulin receptor phosphorylation, insulin receptor was precipitated using protein A/G agarose (Santa Cruz Biotechnology; Santa Cruz, Calif.).

ELISA

Serum Gpc4 was assessed by ELISA (USCNK Life Science; Houston, Tex.), using 50 μl murine or human serum following to the manufacturer's recommendation.

ΔGpc4 Purification

ΔGpc4 was purified from conditioned Opti-MEM of ΔGpc4 overexpressing 3T3-L1 cells. Medium from shScr cells was used as control. After 48 hours, 400 ml medium was pooled and concentrated to 50 ml, dialyzed against PBS/10% glycerol and incubated with 500 μl Ni-NTA agarose (Qiagen; Hilden, Germany) overnight. ΔGpc4 was eluted in 300 mM NaCl, 50 mM NaH3PO4, 10 mM imidazole, 0.05% Tween (pH8.0) containing 250 mM imidazole. Eluates were dialyzed overnight to PBS/10% glycerol and concentrated with Centricon filters to 150 μl.

Serum Proteoglycan Purification

Anion exchange chromatography was performed as described (31), dialyzed against PBS/10% glycerol, concentrated using Centricon filters (Millipore; Bellerica, Mass.) to 50 μl and analyzed by SDS-PAGE.

Mass Spectrometry

Serum proteoglycan preparations from 5 four month-old male C57BL/6 mice were reduced and denatured in buffer containing 2.5% β-mercaptoethanol and resolved on 4-12% gradient acrylamide gels (Invitrogen; Grand Island, N.Y.). Gels were stained with Safestain (Invitrogen), and the gel fragment between 30-75 kDa was submitted for mass spectrometric analysis to the Joslin Proteomics Core Facility.

Insulin Binding Assay $^{125}$I insulin (MP Biomedicals; Santa Ana, Calif.) binding to adherent cells was measured as previously described and as known by one of ordinary skill in the art (32).

Statistical Analysis

Statistical analysis was performed using GraphPad Prism (San Diego, Calif.) and presented as mean±SEM. Significance was tested with unpaired t-test, one-way or two-way ANOVA. A p-value <0.05 was considered significant. Multivariate regression analysis was performed using StatView (Cary, N.C.).

Results

Gpc4 Expression in Fat of Humans Correlates with Body Fat Content and Insulin Sensitivity It was previously shown that Gpc4 is differentially expressed between visceral and subcutaneous fat in rodents and humans, and that expression in adipose tissue of humans is strongly correlated with BMI and WHR (8). Further analysis revealed that Gpc4 expression in subcutaneous fat was markedly decreased in both males and females when comparing lean (BMI<25) to overweight (BMI25-25) and obese (BMI>30) subjects (FIG. 1A). In contrast, expression of Gpc4 in visceral fat was increased in overweight and obese males and females. When grouped by BMI, Gpc4 expression in visceral adipose tissue was highest in overweight subjects with high visceral fat, defined by a CT or MRI ratio between subcutaneous and visceral fat areas >0.4. Interestingly, in both females and males, this relationship was bell-shaped with the highest levels of Gpc4 expression in overweight individuals with a visceral fat distribution and lower levels in individuals with frank visceral obesity, who expressed Gpc4 at almost the same levels as lean individuals.

Multiple clinical parameters differed between these groups (Table 3). Therefore multivariate analysis was performed of Gpc4 expression in visceral and subcutaneous fat versus 14 different clinical parameters that revealed a significant negative correlation of subcutaneous Gpc4 expression with WHR, and a negative correlation of Gpc4 expression in visceral fat with glucose infusion rate (GIR) during euglycemic hyperinsulinemic clamps (Table 1). These correlations were independent from the association of Gpc4 expression with body fat content and distribution, suggesting a link between Gpc4 expression and insulin sensitivity.

Gpc4 Expression in Fat of Rodents at the mRNA and Protein Level

Figure 8:
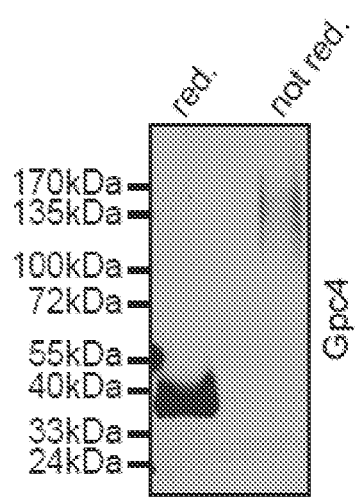
FIG. 8 shows a Western blot for Gpc4 from purified Gpc4 under reduced (red.) or not reduced (not. red.) conditions.

It was previously shown that in mice Gpc4 mRNA expression is two-fold higher in perigonadal than in subcutaneous fat (8). To better understand Gpc4 physiology in the rodent, a peptide antibody against murine Gpc4 was raised and used this to assess Gpc4 protein levels in tissues and serum of mice. As expected, Western blots of extracts from 3T3-L1 preadipocytes run under non-reducing conditions for native Gpc4 revealed a broad smear from ~100 kDa to >170 kDa, representing the 63 kDa core protein with the attached heparan sulfate chains of varying lengths (FIG. 8). As previously described and as known by one of ordinary skill in the art, the core protein of Gpc4 undergoes furin-mediated cleavage creating two disulfide-linked subunits of Gpc4 (11). Thus, when these same extracts were run under reducing conditions, the proteolytically cleaved N-terminal α-subunit of Gpc4 was detected as a sharp band at 37 kDa, allowing more precise quantitation (FIG. 8).

Using this assay, it was found that the difference in expression of Gpc4 between the murine fat depots was even more marked at the protein than at the mRNA level, and that perigonadal fat had ~5-fold higher Gpc4 levels than subcutaneous and brown adipose tissue (FIG. 1B). As in humans, Gpc4 expression in perigonadal fat of mice showed a bell-shaped relationship with level of obesity with upregulation of Gpc4 expression in mice with mild obesity due to high fat diet (HFD), and lower levels in the very obese db/db mice. In subcutaneous fat, Gpc4 expression was also increased in HFD fed mice and increased even further in db/db mice in this depot. This regulation by obesity state was specific to white adipose tissue with no change in Gpc4 in brown adipocyte tissue (BAT) in either the HFD or db/db mice (FIG. 1C).

Role of Gpc4 in Adipocyte Differentiation and Insulin Signaling

Figure 2:
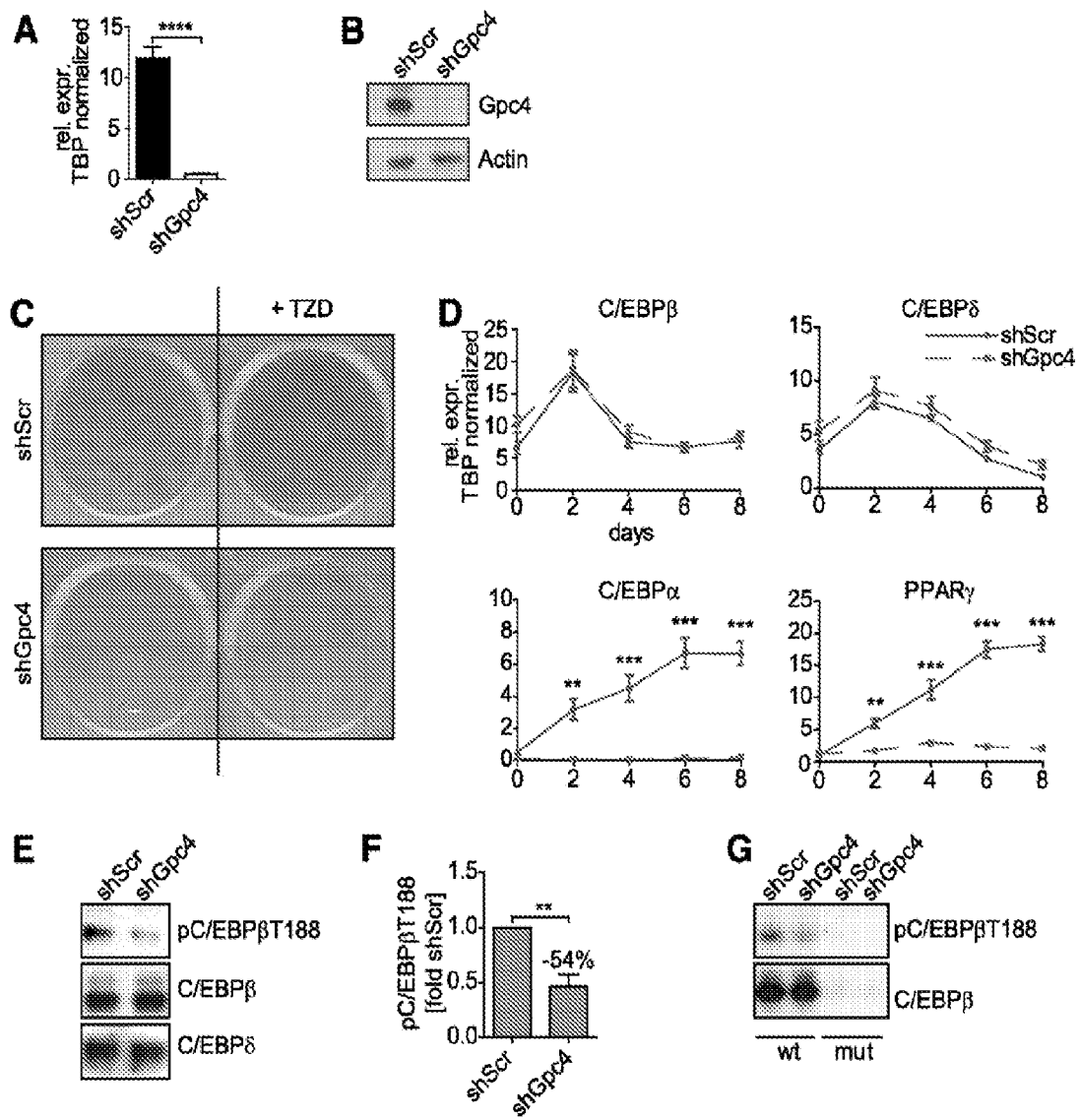
FIG. 2 shows Gpc4 is essential for adipocyte differentiation. A: qPCR for Gpc4 from shGpc4 and control 3T3-L1 cells (n=9). B: Western blot for Gpc4 and actin as loading control, from control and shGpc4 3T3-L1 preadipocytes. C: Oil Red O staining of shScr and shGpc4 cells at day 8 of differentiation with or without troglitazone (TZD). D: qPCR for key transcription factors of adipocyte differentiation during 8 days of differentiation (n=9). E: Western blots from nuclear extracts of shScr and shGpc4 cells 24 h after induction of differentiation. F: Quantification of phospho-C/EBPβ on Thr188 normalized to total C/EBPβ (n=3), 24 h after induction. G: Western blots from oligonucleotide pull downs with a wild-type C/EBP binding motif (wt) or a mutant that is not bound by C/EBPβ as control (mut) 24 h after induction of differentiation. P<0.01; *P<0.001; ****P<0.0001.

To better understand the functional link between Gpc4 and adipogenesis 3T3-L1 preadipocytes were created with stable knockdown of Gpc4 using lentivirally-expressed shRNA (shGpc4). This resulted in a >95% depletion of Gpc4 mRNA (FIG. 2A) and a reduction of Gpc4 protein below the limits of detection when compared to control cells infected with scrambled shRNA (shScr) (FIG. 2B). The control 3T3-L1 cells differentiated efficiently into adipocytes within eight days after induction as visualized by Oil Red O (FIG. 2C). In contrast, Gpc4 knockdown cells failed to accumulate lipids. Furthermore, while stimulation by thiazolidinediones enhanced the differentiation of control cells, this had no significant effect on shGpc4 cells (FIG. 2C).

Figure 9:
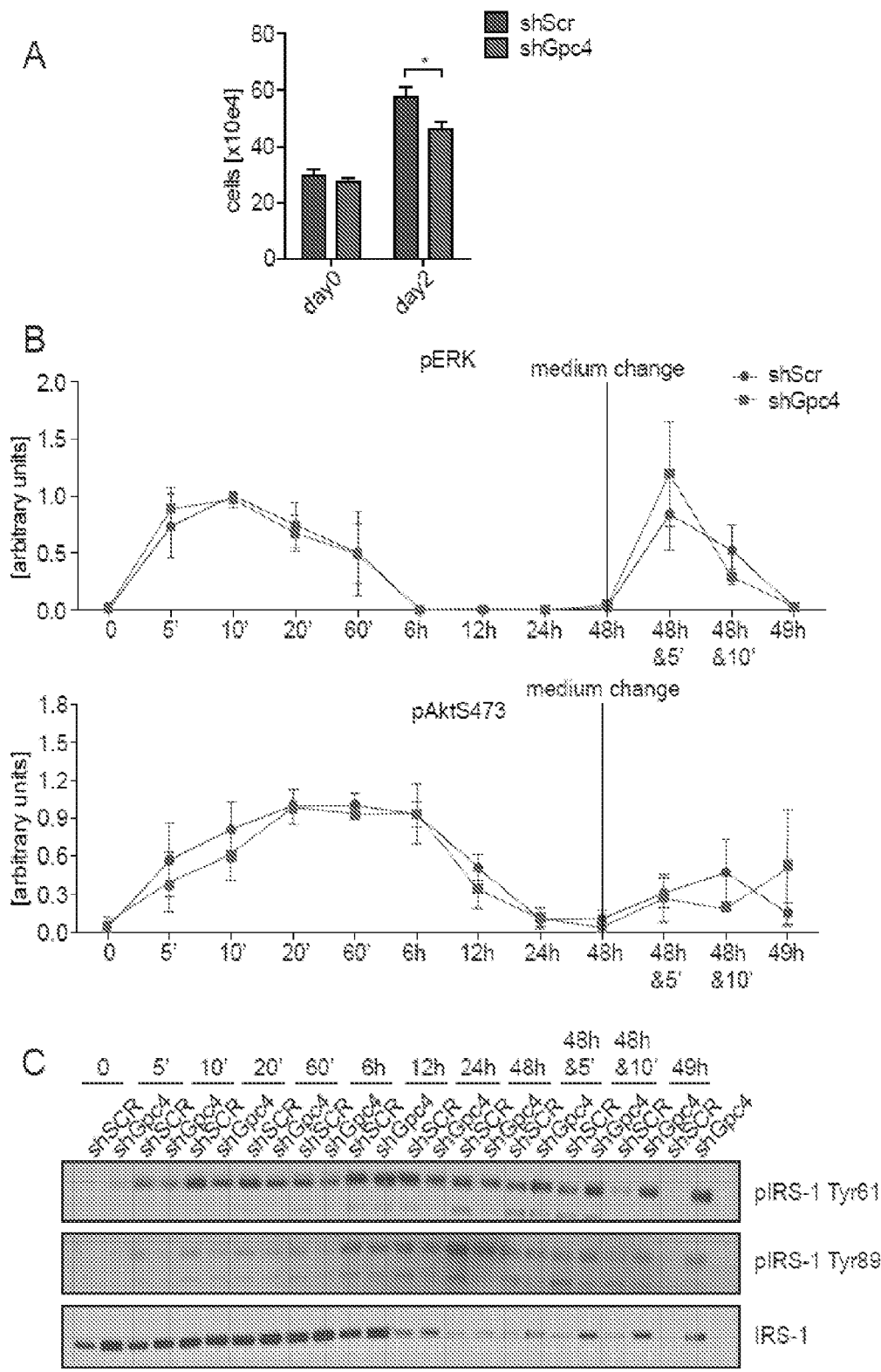
FIG. 9 shows (A) Cell number of control and shGpc4 3T3-L1 at day 0 and day 2 of differentiation (n=3). (B) Quantification of Western blots for ERK and AktS473 phosphorylation during the first 49 hours of differentiation. Phospho-signals were normalized to total ERK and Akt, respectively. Induction medium was changed after 48 hours to growth medium containing 10% FBS and 170 nM insulin (n=3). (C) Western Blot for pIRS-1Y612 and pY896 and total IRS-1. Differentiation was induced at time point 0. Induction medium was changed to growth medium after 48 hours.

Failure to accumulate lipids was due to a blockade in differentiation. qPCR revealed that Gpc4 knockdown cells induced early adipogenic markers C/EBPβ and C/EBPδ at levels comparable to control. By contrast, treatment of knockdown cells with induction cocktail did not induce the key downstream transcription factors for adipogenesis C/EBPα and PPARγ, which were robustly increased in control cells (FIG. 2D) (14). Western blots from nuclear extracts 24 h after induction confirmed similar protein levels of C/EBPβ and C/EBPδ between control and knockdown cells (FIG. 2E), however, the important regulatory phosphorylation of C/EBPβ Thr188 was reduced 54% in Gpc4 knockdown cells compared to controls (FIG. 2E-F). Pull-downs from nuclear lysates from these cells with oligonucleotides containing a C/EBP binding site revealed similar binding of C/EBPβ from control and shGpc4 cells, however the bound C/EBP from Gpc4 knockdown cells showed greatly reduced Thr188 phosphorylation indicating diminished activation of this key transcription factor (FIG. 2G). In addition to its role as activator of C/EBPα and PPARδ transcription, C/EBPβ is essential for clonal expansion in 3T3-L1 preadipocytes (15), and consistent with the diminished phosphorylation/activation of C/EBPβ reduced mitotic clonal expansion in knockdown cells was also observed (FIG. 9A).

Phosphorylation of C/EBPβ on Thr188 is mediated by MAPK and PI3-Kinase signaling (16). Assessment of the phosphorylation/activation of ERK and Akt during the first 49 h of differentiation revealed a tendency for lower AktS473 phosphorylation, but no alterations of ERK phosphorylation (FIG. 9B). Phosphorylation of IRS-1 on Y612 and Y896, sites required for insulin-mediated Akt and ERK activation, showed reduced phosphorylation, suggesting an effect of Gpc4 deletion on insulin signaling (FIG. 9C).

Figure 3:
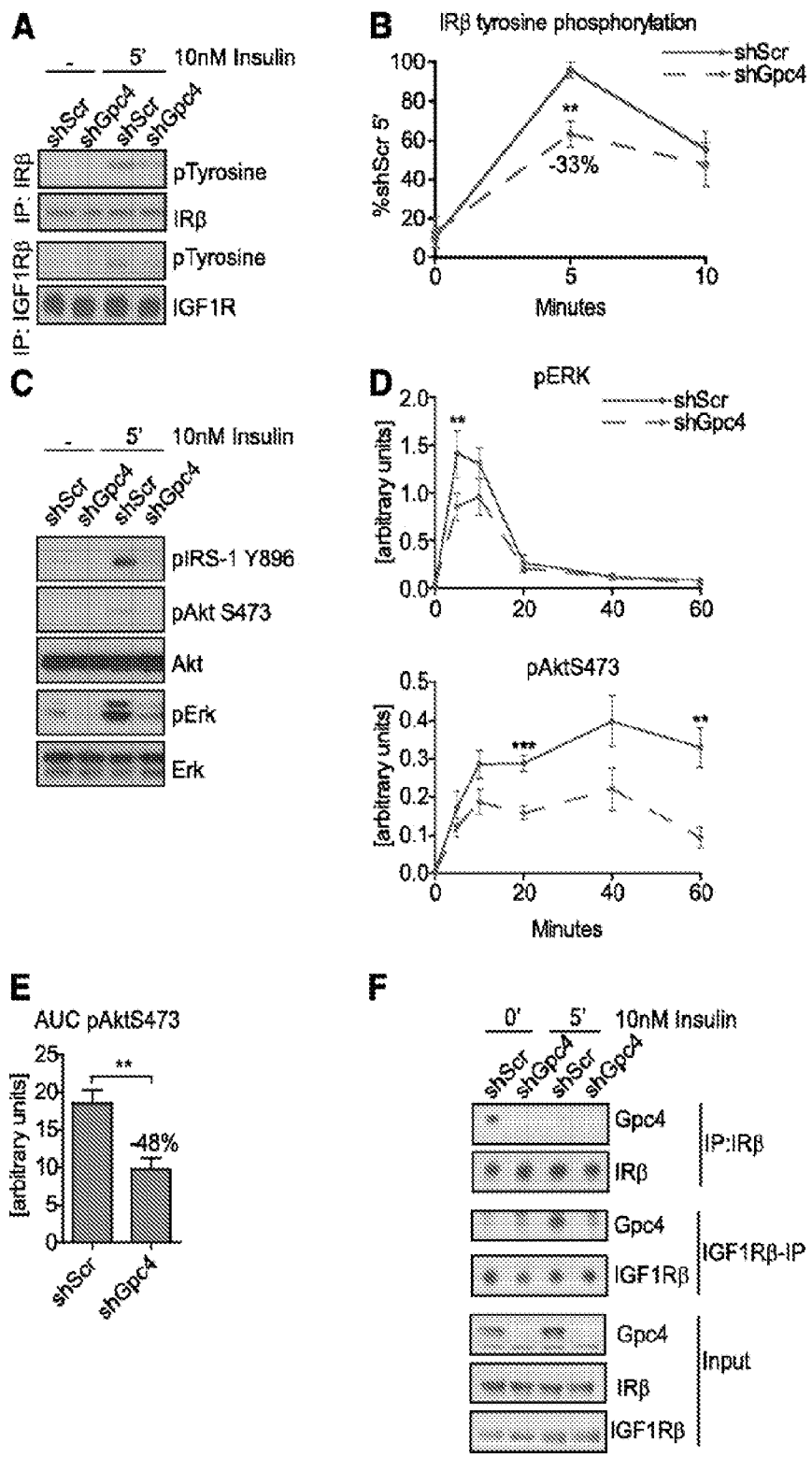
FIG. 3 shows Gpc4 regulates insulin receptor activation and downstream signaling. A: Western blots from insulin- and IGF1R β-subunit immunoprecipitations of confluent shScr and shGpc4 preadipocytes, blotted for insulin/IGF1R β and pTyrosine before and after 5 min of 10 nmol/L insulin stimulation. B: Quantification of tyrosine phosphorylated insulin receptor in 3T3-L1 preadipocytes, normalized to total insulin receptor levels (n=6). C: Western blots of confluent shScr and shGpc4 preadipocytes from total cell lysates before and after 5-min stimulation with 10 nmol/L insulin. D: Quantification of ERK and AktS473 phosphorylation at 0, 5, 10, 20, 40, and 60 min after insulin stimulation. pERK and pAktS473 were normalized to total ERK and Akt levels (n=8). E: Area under the curve of AktS473 phosphorylation shown in D. F: Coimmunoprecipitation of Gpc4 with insulin and IGF1R β-subunit in 3T3-L1 cells. For all stimulation experiments, confluent undifferentiated preadipocytes were serum-starved for 3 h and stimulated with 10 nmol/L insulin. P<0.01; *P<0.001.

Insulin stimulation of 3T3-L1 preadipocytes revealed 33% reduction in insulin receptor and reduced IGF1R phosphorylation of Gpc4 knockdown cells compared to control (FIG. 3A-B). The reduced IR/IGF1R activation resulted in a reduction of IRS-1 phosphorylation and a 40-45% reduction in ERK activation ($p<0.01$) and phosphorylation of Akt on Ser473 ($p<0.001$) in Gpc4 knockdown cells (FIG. 3C-D). This was not caused by reduced insulin binding, as shGpc4 preadipocytes showed higher binding of the $^{125}$I insulin tracer, but lower affinity as judged by a rightward shift of the competition curve by unlabeled insulin (FIG. 10A). Furthermore, AktS473 phosphorylation declined more rapidly in the Gpc4 knockdown cells during the 60 minute time course (FIG. 3D) resulting in a ~50% reduction of AktS473 phosphorylation over the time course in Gpc4 knockdown cells as quantified by the area under the curve (FIG. 3E). This decreased AktS473 and ERK phosphorylation in Gpc4 depleted cells was observed in a wide range of insulin concentrations (FIG. 10B). However, these changes were specific to insulin and not observed after stimulation with 10% FBS (FIG. 10C).

Gpc4 Interacts with the Insulin Receptor and Enhances Adipocyte Differentiation Independent of Membrane Anchorage Gpc4 does not possess transmembrane or intracellular domains but is anchored to the cell membrane via a GPI anchor. Thus, Gpc4 itself cannot signal, but mediates its intracellular functions via interaction with other transmembrane proteins. Since depletion of Gpc4 resulted in reduced insulin/IGF1 receptor activation (FIG. 3A-B) a possible interaction of Gpc4 was tested for with these receptors by performing co-immunoprecipitation experiments. This revealed co-immunoprecipitation of Gpc4 with the insulin receptor under basal growth conditions, which was lost upon insulin stimulation, indicating that Gpc4 interacts with the unoccupied insulin receptor, but dissociates upon insulin binding and receptor activation. Interestingly, interaction with the IGF1R showed a reciprocal pattern, as Gpc4 associated with the IGF1R after, but not prior to, insulin stimulation (FIG. 3F).

Figure 4:
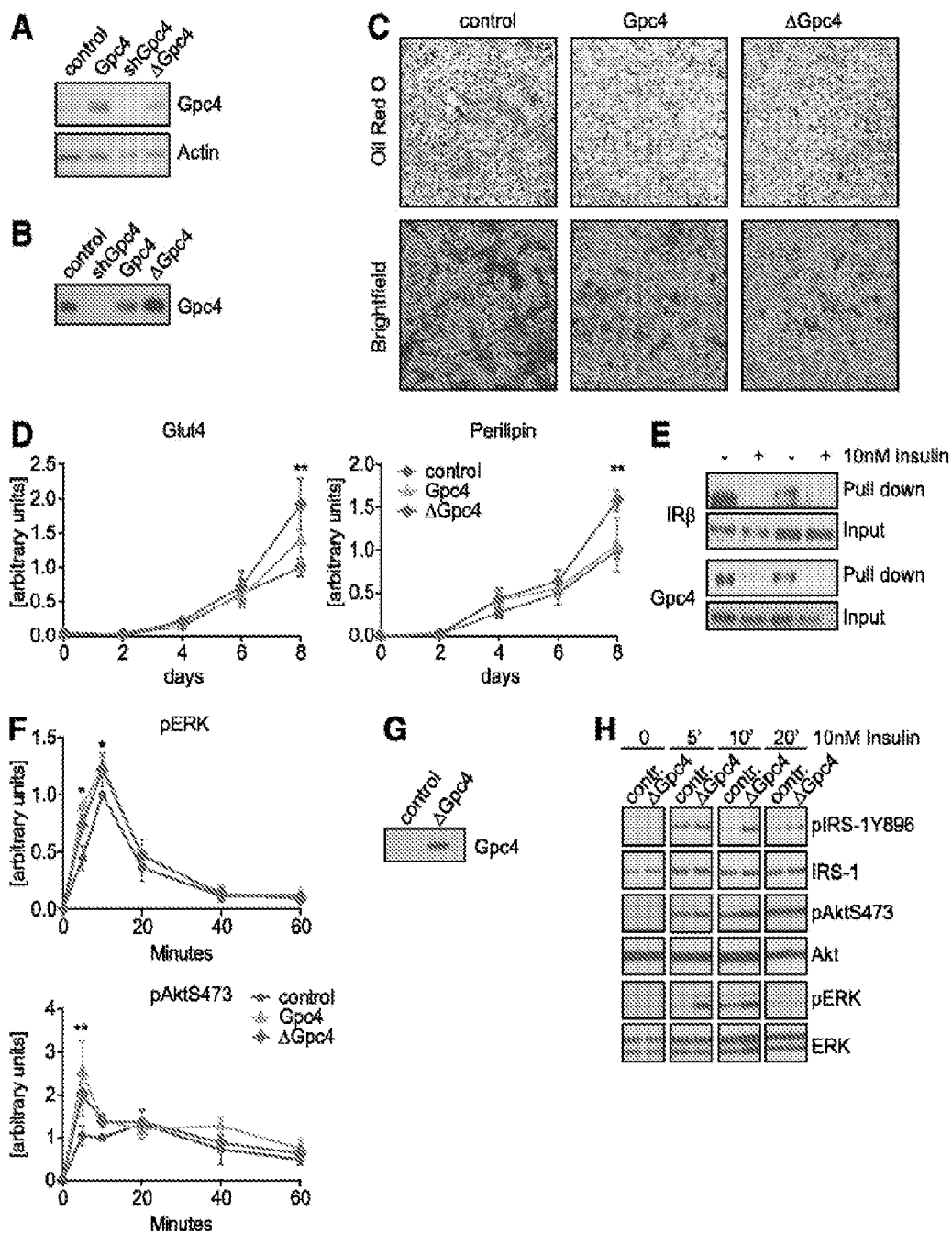
FIG. 4 shows overexpression of Gpc4 enhances adipocyte differentiation and insulin signaling. A: Western blot for Gpc4 of 3T3-L1 stably infected with control lentivirus, native Gpc4, shGpc4, or ΔGpc4. In the ΔGpc4 mutant, the GPI attachment motif 529SAG531 was replaced with a 6xHis-tag [SEQ ID NO: 9]. Actin was used as loading control. B: Western blot for Gpc4 from serum-free Opti-MEM conditioned for 24 h by the indicated cell lines. C: Oil Red O staining and brightfield images from control, Gpc4, and ΔGpc4 expressing cells taken at day 8 of differentiation. D: qPCR for Glut4 and perilipin during an 8-day time course of differentiation of control, Gpc4, and ΔGpc4 overexpressing cells. **Indicates significantly higher expression in ΔGpc4 versus control cells (n=5). E: Ni-NTA pull downs of His-tagged ΔGpc4 from total cell lysates during normal growth conditions or after 5 min of 10 nmol/L insulin stimulation. F: Quantification of ERK and AktS473 phosphorylation at 0, 5, 10, 20, 40, and 60 min after 10 nmol/L insulin stimulation of confluent 3T3-L1 preadipocytes. pERK and pAktS473 were normalized to total ERK and Akt levels (n=3). G: Western blot for Gpc4 of purified ΔGpc4 and control eluate. H: Insulin stimulation in presence or absence of purified recombinant ΔGpc4. Cells were pretreated with ΔGpc4 or control eluate during the 1-h serum starvation before 10 nmol/L insulin stimulation. All samples were run on one SDS gel; time points were separated for better visualization. *P<0.05; **P<0.01.

White adipose tissue is an endocrine organ secreting various adipokines, regulating metabolic function and glucose homeostasis (5). Glypicans can be released from the cell surface by cleavage of the GPI anchor (17). To determine if Gpc4 is released from adipocytes and acts as a soluble modulator of insulin signaling, 3T3-L1 cell lines were created with stable overexpression of native Gpc4 and a soluble mutant form of Gpc4 lacking the GPI anchor attachment site (ΔGpc4). Western blots confirmed moderate overexpression of native Gpc4 and ΔGpc4 (FIG. 4A). Analysis of conditioned medium confirmed Gpc4 protein in the medium of ΔGpc4 cells, as well as smaller amounts of Gpc4 in the medium of control and cells overexpressing wild-type Gpc4, demonstrating that endogenous Gpc4 is released from the cell surface to the medium (FIG. 4B). Overexpression of Gpc4 or ΔGpc4 opposed the results of Gpc4 depletion during adipocyte differentiation with slightly increased Ppar𝛾 and C/EBPα expression and C/EBPβ phosphorylation compared to control cells (FIG. 11A-B). This led to an increased adipocyte differentiation when compared to control cells (FIG. 4C). Interestingly, overexpression of ΔGpc4 also resulted in enhanced adipocyte differentiation indicating that membrane anchorage is not required for the pro-adipogenic effect of Gpc4. Expression of perilipin and Glut4, both markers of mature adipocytes, were also significantly increased after differentiation of ΔGpc4 cells and trended towards being increased expression in Gpc4 overexpressing cells (FIG. 4D).

To determine if soluble ΔGpc4 could interact with the insulin receptor, His-tagged-ΔGpc4 pulled-down using Ni-NTA agarose from cell lysates with or without insulin stimulation (FIG. 4E). Similarly to endogenous membrane-anchored Gpc4, the insulin receptor co-precipitated with ΔGpc4 under basal conditions, but this interaction was lost upon insulin stimulation. Interestingly, ΔGpc4 was not pulled-down after insulin stimulation, indicating that not only is Gpc4 binding to the insulin receptor abolished upon insulin stimulation, but the sequestration of ΔGpc4 to the cell surface is lost.

Depletion of Gpc4 resulted in reduced insulin signaling. Overexpression of native Gpc4 or ΔGpc4 enhanced insulin-stimulated ERK (100% and 67%, respectively) and Akt-Ser473 (140% and 94%, respectively) peak phosphorylation (FIG. 4F) and Gpc4 increased 2-deoxy glucose uptake by cells (FIG. 11C). Furthermore when 3T3-L1 cells were pretreated with affinity purified Gpc4 or control eluate during serum starvation (FIG. 4G), Gpc4 enhanced ERK, Akt and IRS-1Y896 phosphorylation, after stimulation with insulin (FIG. 4H).

Figure 5:
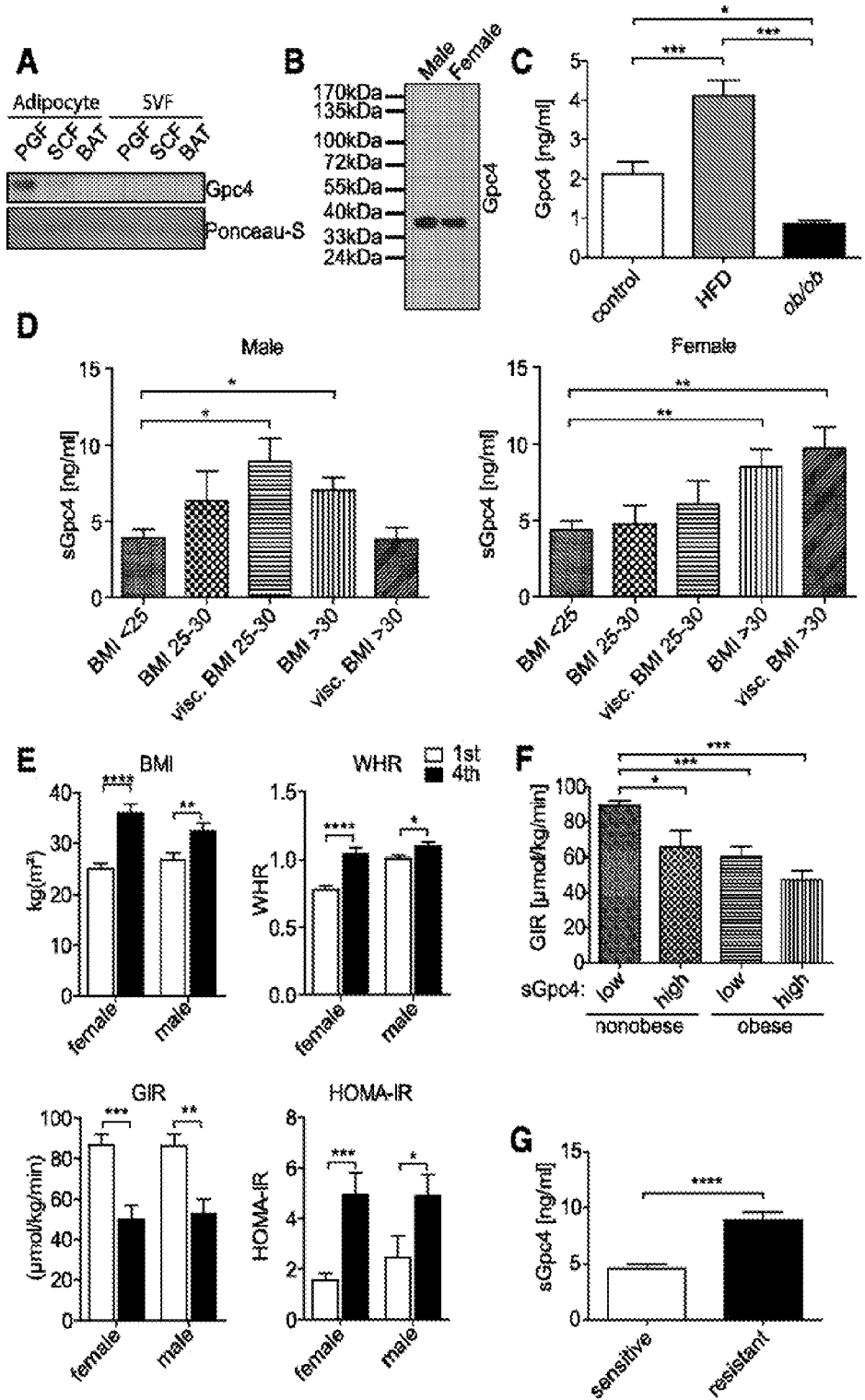
FIG. 5 shows Gpc4 is released from adipocytes and correlates with markers of body fat and insulin resistance. A: Western blot for Gpc4 from conditioned serum-free Opti-MEMI of cultured isolated subcutaneous, perigonadal, and brown adipocytes and the corresponding SVF. Ponceau-S staining shows equal loading of proteins. Cells were isolated by collagenase digest and medium was conditioned for 12 h. B: Western blot of serum Gpc4. Glycoproteins from serum of 4-month-old C57BL/6 male and female mice were purified using anion exchange chromatography. Western blots from concentrated eluates were probed for Gpc4. C: Gpc4 ELISA from serum of C57BL/6 mice fed an HFD for 8 weeks, ob/ob and control mice. Control mice are C57BL/6 chow diet-fed mice and ob/+ mice combined (n=6 per genotype). D: Gpc4 ELISA from serum of nondiabetic females (n=77) and males (n=83) grouped according to BMI and body fat distribution. Visceral overweight and obesity is defined by a CT or MRI ratio >0.4 between subcutaneous and visceral fat areas. E: Comparison of BMI, WHR, and GIR during a euglycemic hyperinsulinemic clamp and HOMA-IR of the lowest and highest quartile of serum Gpc4 levels of females and males (n=19 and 20 per quartile, respectively). F: Comparison of GIR from nonobese (BMI <30) and obese (BMI >30) subjects divided into groups with low serum Gpc4 levels (≤5 ng/mL) and high serum Gpc4 levels (≥9 ng/mL). G: Serum Gpc4 levels in 30 obese age-, sex-, and BMI-matched insulin-sensitive and insulin-resistant subjects. *P<0.05; P<0.01; *P<0.001; ****P<0.0001.
Figure 12:
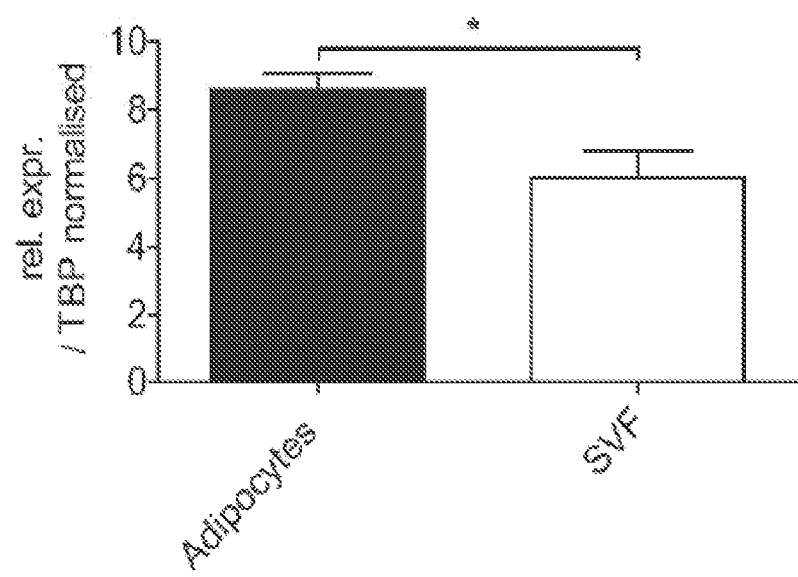
FIG. 12 shows qPCR for Gpc4 from freshly isolated perigonadal adipocytes and the corresponding SVF. Gpc4 expression was normalized to TBP (n=3).
Figure 13:
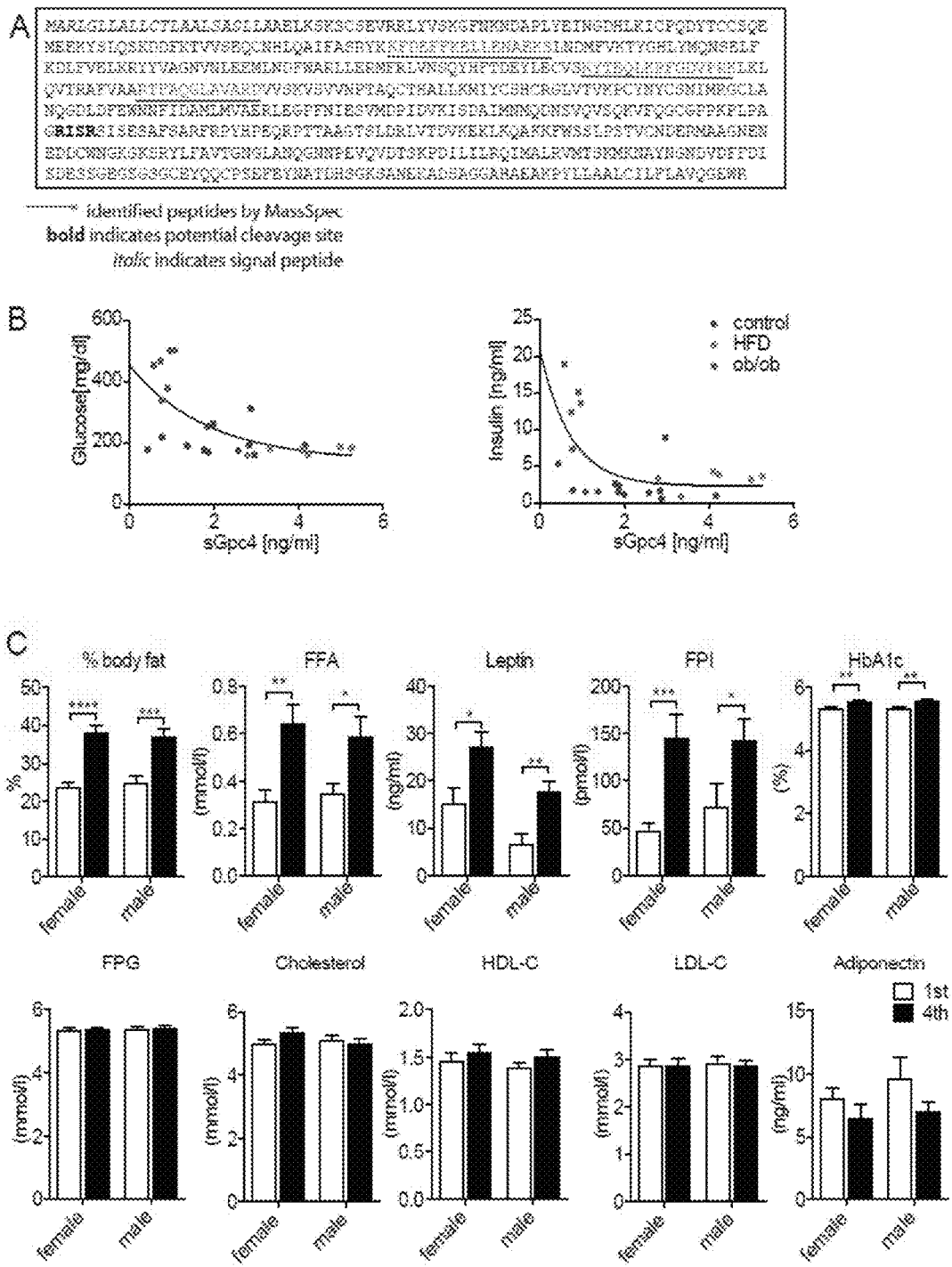
FIG. 13 shows (A) Murine Gpc4 protein sequence. Peptides identified by mass spectrometry are underlined. (B) Correlation between serum Gpc4 and glucose and insulin levels in control, HFD fed (8 weeks) and ob/ob mice. (C) Comparison of clinical parameters from the lowest and highest quartile of serum Gpc4 levels of 160 patients shown in FIG. SD (n=40 per quartile).

Gpc4 is Released from Adipose Tissue and is a Circulating Marker for BMI and Insulin Resistance To determine if Gpc4 can be released from adipocytes into the circulation adipocytes were separated from the SVF of subcutaneous, perigonadal and brown fat, cultured them in vitro, and assayed the media for Gpc4 by Western blotting. The release of Gpc4 from intra-abdominal (perigonadal) adipocytes was greater than that of subcutaneous adipocytes, and there was no release from either SVF or brown adipocytes (FIG. 5A). Gpc4 mRNA expression was also significantly higher in isolated perigonadal adipocytes compared to the corresponding SVF (FIG. 12). To determine if Gpc4 is also released in vivo, glycoproteins were purified from mouse serum and assayed these samples by Western blotting for Gpc4. As shown in FIG. 5B, Gpc4 was detected in sera from both male and female C57BL/6 mice. Mass spectrometric analysis confirmed this with three tryptic peptides for Gpc4 (FIG. 13A). ELISA assays for Gpc4 revealed circulating levels of around 2 ng/ml in lean C57B1/6 and ob/+ mice, which increased to ~4 ng/ml in mice subjected to eight weeks of HFD feeding, mirroring the gene expression data. Serum Gpc4 levels were ~1 ng/ml in the markedly obese ob/ob mice (FIG. 5C). Fed blood glucose and insulin measurements revealed that HFD fed mice were still able to maintain normal glycemia and normal insulinemia, with much higher serum Gpc4 levels than controls, whereas ob/ob mice had elevated blood glucose levels despite hyperinsulinemia, which was accompanied with reduced serum Gpc4 levels (FIG. 13B).

Figure 14:
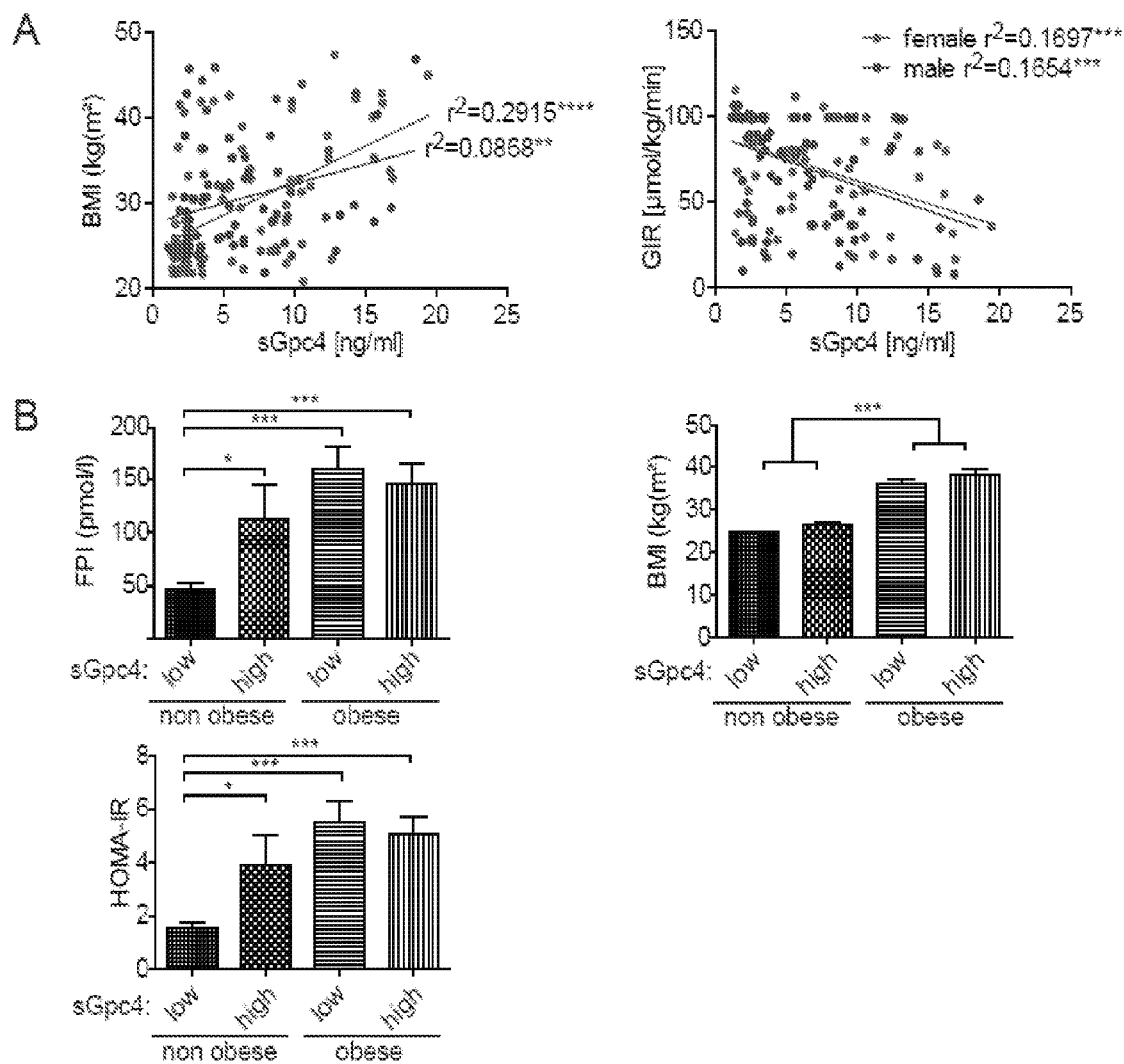
FIG. 14 shows (A) Correlation of serum Gpc4 with BMI and GIR in non-diabetic females (n=77) and males (n=83). (B) Comparison of HOMA-IR and BMI from non-obese (BMI<30) and obese (BMI>30) subjects divided into groups with low serum Gpc4 levels (<5 ng/ml) and high serum Gpc4 levels (>9 ng/ml).

To determine if Gpc4 was circulating in humans, a human Gpc4 ELISA assay was utilized to assess serum Gpc4 levels in the same cohort that had been used for expression analysis of Gpc4 mRNA in adipose. In males serum Gpc4 levels paralleled the gene expression data from visceral fat (FIG. 5D), with the highest serum Gpc4 levels in individuals who were overweight with a visceral distribution and lower levels in both lean and viscerally obese subjects. By contrast, females showed a continuous increase in serum Gpc4 levels from lean to overweight and obese. When both male and female subjects were divided into the lowest and highest quartile of serum Gpc4 levels, those individuals with highest serum Gpc4 had significantly higher percentage body fat, higher BMI, larger WHR and higher levels of free fatty acids and leptin, all markers of body fat content. Additionally, high serum Gpc4 was associated increased markers of insulin resistance, including high HOMA-IR, high fasting plasma insulin and insulin resistance as assessed by decreased GIR (FIG. 5E and FIG. 13C). Association was not observed with fasting-plasma-glucose, cholesterol, HDL-C, LDL-C or serum adiponectin, although in this group of non-diabetics, those with high serum Gpc4 did have significantly higher HbA1c values, although still within the normal range (FIG. 13C). Multivariate analysis of 15 parameters including Gpc4 expression in subcutaneous and visceral fat confirmed a positive correlation of BMI and a negative correlation of GIR with serum Gpc4 levels (Table 2 and FIG. 14A). When subjects were divided into subgroups of non-obese and obese subjects with either low serum Gpc4 (<=5 ng/ml) or high serum Gpc4 (>=9 ng/ml), non-obese subjects with high serum Gpc4 levels showed the same degree of insulin resistance, measured by fasting plasma insulin, GIR and HOMA-IR, as obese subjects with either low or high serum Gpc4 levels (FIG. 5F and FIG. 14B). In an independent set of 30 age-, gender- and BMI-matched obese insulin sensitive and insulin resistant patients (18), ~2 times higher sGpc4 levels was observed in insulin resistant compared to insulin sensitive patients (FIG. 5G).

Blunted Insulin Secretion in Glypican-4 Knockout Mice

Figure 7:
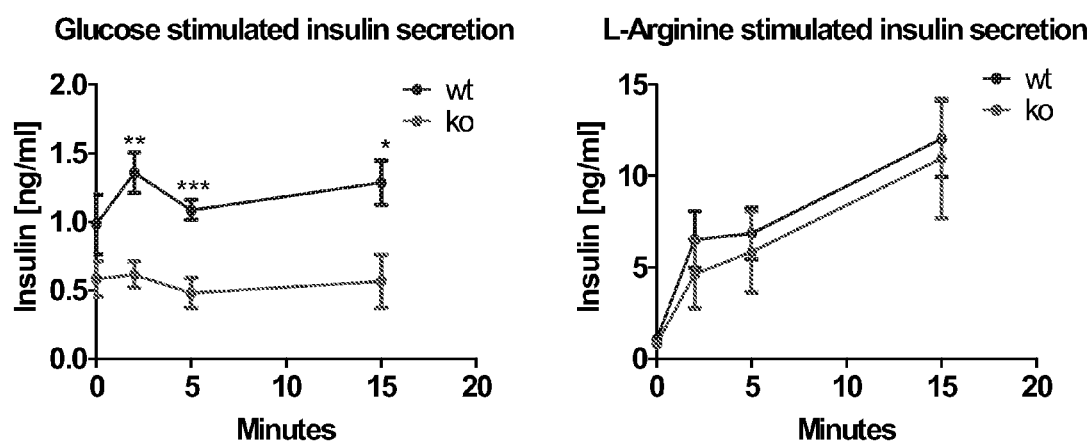
FIG. 7 shows that Glypican-4 not only modulates insulin receptor affinity and is a serum marker for insulin resistance, as shown in the previous publication, but also regulates the secretion of insulin from pancreatic beta cells.

Further, to test insulin secretion from pancreatic beta cells, Glypican-4 wild type and knockout mice were intraperitoneally injected with a bolus of glucose or 1-arginine and serum insulin levels measured at 2', 5' 10' and 15' post injection. Glypican-4 knockout animals had a blunted insulin secretion upon glucose injection, but not upon administration of 1-arginine, indicating that Glypican-4 knockout beta cells are (i) generally capable to secrete insulin, but show a specific glucose sensing defect. These data indicate that Glypican-4 not only modulates insulin receptor affinity and is a serum marker for insulin resistance, as shown in the previous publication, but also regulates the secretion of insulin from pancreatic beta cells. See, FIG. 7.

Discussion

Glypican-4 belongs to the family of GPI-anchored heparan sulfate proteoglycans, which includes six members in mammals (10). It was previously found that Gpc4 is differentially expressed between fat depots and is highly regulated in obesity (8). The present invention shows that Gpc4 regulates insulin signaling via interaction with the insulin receptor. As a result, reducing levels of Gpc4 diminishes insulin signaling. In preadipocytes, this results in blunted activation of C/EBPβ and a block in adipocyte differentiation. The present invention also demonstrates that Gpc4 is released from adipose tissue and that circulating Gpc4 in rodents and humans positively correlates with body fat content and insulin resistance.

Expansion of visceral adipose tissue, i.e., central obesity, is associated with insulin resistance, whereas expansion of subcutaneous adipose tissue, i.e., peripheral obesity, is not (7, 5). Defining the mechanisms underlying body fat distribution and this differential link to insulin resistance is important for understanding the development of comorbidities associated with obesity, including type 2 diabetes, stroke, hypertension and cardiovascular disease (19). The present invention shows that expression of Gpc4 is not only differential between subcutaneous and visceral fat, but that Gpc4 expression in visceral adipose positively correlates with both BMI and, independently, with insulin resistance as measured by euglycemic, hyperinsulinemic clamps. Of greater significance, Gpc4 is present in serum of mice and humans, and serum Gpc4 levels are positively correlated with body fat content and insulin resistance. In non-diabetics, serum Gpc4 increases progressively with BMI, especially in viscerally obese women and viscerally overweight males. Multivariate analysis revealed an independent negative correlation of serum Gpc4 with GIR, i.e., thus higher serum Gpc4 levels are associated with greater insulin resistance. Indeed, non-obese subjects (BMI<30) with high serum Gpc4 (≥9 ng/ml) levels have the same degree of insulin resistance by euglycemic clamp, fasting insulin and HOMA-IR as obese subjects, independent of serum Gpc4 levels. Furthermore sGpc4 levels are doubled in insulin resistant obese subjects compared to age-, gender- and BMI-matched insulin sensitive subjects. Thus serum Gpc4 is not only a marker for BMI, it is an independent marker of insulin resistance.

Figure 15:
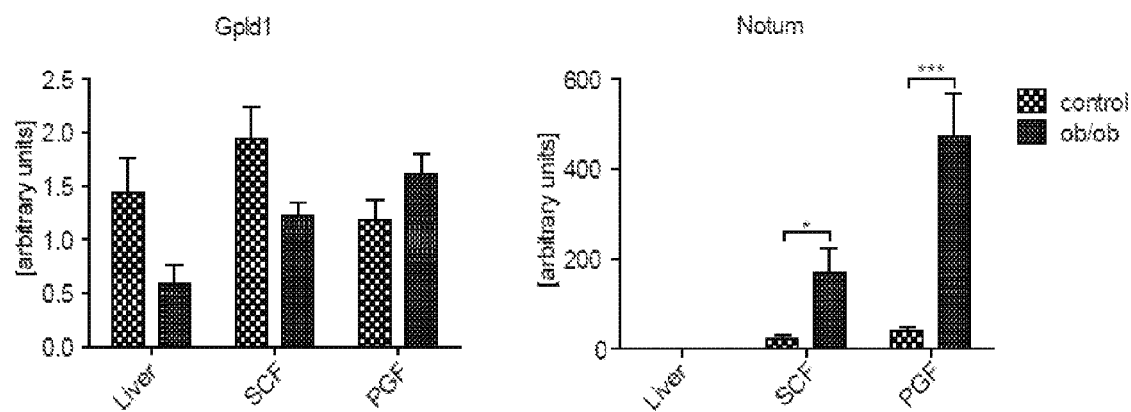
FIG. 15 shows Real Time PCR for the GPI lipases Gpld1 and Notum in liver, subcutaneous (SCF) and perigonadal fat (PGF) of control (ob/+) and ob/ob mice. Expression values were normalized to TBP (n=6).

This link between Gpc4 and changes in insulin sensitivity appears to involve two novel mechanisms. First, glypicans are released from the cell surface by an enzymatically regulated process mediated by GPI-lipases. Glycosylphosphatidylinositol-specific phospholipase D (GPLD1) has been suggested to cleave Gpc4 (17, 20) and its activity is regulated by insulin (21, 22). Similar to Gpc4, GPLD1 levels in serum are increased upon feeding a high sucrose diet (23), but decreased in ob/ob mice (24). This could explain the lack of direct correlation between expression of Gpc4 in fat and serum Gpc4 levels. The present invention did not find change in Gpld1 expression in adipose tissue of ob/ob mice, but another GPI lipase, Notum, increased (FIG. 15). In addition Gpc4 is widely expressed with highest expression in kidney, pituitary and white adipose tissue, indicating that other tissues could contribute to serum Gpc4. However the strong association of serum Gpc4 levels with BMI in humans and the fact that Gpc4 can be released from cultured primary adipocytes make adipose tissue one likely source of serum Gpc4.

To date, no circulating factor has been shown to directly enhance the activation of the insulin receptor itself. Both the transmembrane glycoprotein PC-1/ENPP-1 and circulating alpha 2-HS glycoprotein are known to interact with the extracellular domains of the insulin receptor and to negatively affect insulin binding and activation of the insulin receptor (25, 26). By contrast, it was shown that both membrane and non-membrane bound Gpc4 can interact with the insulin receptor and enhance insulin signaling. This interaction occurs with the unoccupied insulin receptor, and stimulation by insulin disrupts the interaction of Gpc4 with the insulin receptor. Thus, overexpression of native Gpc4 or ΔGpc4 or addition of recombinant ΔGpc4 enhances insulin signaling in 3T3-L1 cells, whereas the depletion of Gpc4 results in reduced insulin receptor phosphorylation and downstream signaling.

Insulin is an important regulator of adipocyte differentiation and function (4). In line with that adipocyte differentiation is increased in Gpc4 or ΔGpc4 overexpressing cells and blocked in Gpc4 knockdown cells. The latter is due to an inability to induce C/EBPα and PPARγ the key transcription factors required for differentiation, secondary to reduced phosphorylation of C/EBPβ at the ERK/GSK3β consensus site Thr188. Phosphorylation of Thr188 is essential for DNA binding and transactivation of C/EBPα and PPARγ (16, 27). Block of adipocyte differentiation at this stage of differentiation is also seen in IRS-1/IRS-2 double knockout cells (28) further indicating a link between insulin signaling and the adipocyte differentiation defect. Overexpression of the Akt and ERK inhibitor TRB3 also prevents activation of C/EBPβ and thereby inhibits adipocyte differentiation (29). However, it is possible that Gpc4 could affect additional signaling pathways, or that other factors within the insulin signaling pathway contribute to the differentiation defect, as insulin signaling induces a variety of transcription factors that might regulate adipocyte differentiation (30).

Taken together our data show the novel and non-obvious finding that Gpc4 is an insulin-sensitizing "adipokine" that directly interacts with the insulin receptor to regulate its activation and downstream signaling. The importance of Gpc4 in modulating insulin signaling is underlined by the inability of Gpc4 knockdown cells to differentiate into adipocytes due to a lack of insulin signaling. In addition to its biological activity, serum levels of Gpc4 are correlated with insulin resistance. The role of Gpc4 as an insulin sensitizer and its higher serum levels in insulin resistant individuals may seem counterintuitive at first. However insulin itself shows a similar distribution with lower levels in insulin sensitive versus insulin resistant individuals. Given that GPLD1 is the most likely candidate to cleave Gpc4 and is itself an insulin regulated gene, it is possible that increasing levels of insulin early in obesity lead to increased Gpc4 cleavage resulting in increased circulating Gpc4 levels. With disease progression, as in the ob/ob mouse, increased insulin resistance in GPLD1-producing cells would result in a reduction of GPLD1 activity and a drop in circulating Gpc4 levels, further decreasing insulin sensitivity and accelerating disease progression. Thus, our data suggest that increased circulating Gpc4 levels could be a novel regulatory mechanism by which fat acts to counteract insulin resistance, and maintaining high serum Gpc4 levels in severely insulin resistant or diabetic subjects could lower insulin demands. While further studies will be required to dissect the various function of soluble vs. membrane bound Gpc4, glypican-4 forms a novel adipokine and a novel mechanism by which adipose tissue can modulate insulin signaling.

Equivalents

Those skilled in the art will recognize, or be able to ascertain and implement using no more than routine experimentation, many equivalents of the specific embodiments described herein. Such equivalents are intended to be encompassed by the following claims. Any combinations of the embodiments disclosed in the dependent claims are contemplated to be within the scope of the disclosure.

Incorporation By Reference

The disclosure of each and every US and foreign patent and pending patent application and all publications referred to herein (including in the attached manuscript) are specifically incorporated by reference herein in their entirety.

REFERENCE LIST

1. S. Gesta, Y. H. Tseng, and C. R. Kahn Developmental origin of fat: tracking obesity to its source *Cell.* 131, 242-256 (Oct. 19, 2007)
2. T. T. Tran, Y. Yamamoto, S. Gesta, and C. R. Kahn Beneficial effects of subcutaneous fat transplantation on metabolism *Cell Metab.* 7, 410-420 (2008)
3. S. C. Butterwith Regulators of adipocyte precursor cells *Poult. Sci.* 76, 118-123 (1997)
4. M. Bluher, M. D. Michael, O. D. Peroni, K. Ueki, N. Carter, B. B. Kahn, and C. R. Kahn Adipose tissue selective insulin receptor knockout protects against obesity and obesity-related glucose intolerance *Dev Cell.* 3, 25-38 (2002)
5. Y. Deng and P. E. Scherer Adipokines as novel biomarkers and regulators of the metabolic syndrome *Ann N Y Acad Sci.* 1212, E1-E19 (2010)
6. R. S. Ahima and J. S. Flier Adipose tissue as an endocrine organ *Trends Endocrinol Metab.* 11, 327-332 (2000)
7. S. Kralisch, M. Bluher, R. Paschke, M. Stumvoll, and M. Fasshauer Adipokines and adipocyte targets in the future management of obesity and the metabolic syndrome *Mini. Rev Med Chem.* 7, 39-45 (2007)
8. S. Gesta, M. Bluher, Y. Yamamoto, A. W. Norris, J. Berndt, S. Kralisch, J. Boucher, C. Lewis, and C. R. Kahn Evidence for a role of developmental genes in the origin of obesity and body fat distribution *Proc Natl Acad Sci USA.* 103, 6676-6681 (Apr. 25, 2006)
9. B. De Cat and G. David Developmental roles of the glypicans *Semin. Cell Dev Biol.* 12, 117-125 (2001)
10. A. Fico, F. Maina, and R. Dono Fine-tuning of cell signaling by glypicans *Cell Mol Life Sci.* 68, 923-929 (2011)
11. J. Filmus, M. Capurro, and J. Rast Glypicans *Genome Biol.* 9, 224-2008)
12. S. A. Karumanchi, V. Jha, R. Ramchandran, A. Karihaloo, L. Tsiokas, B. Chan, M. Dhanabal, J. I. Hanai, G. Venkataraman, Z. Shriver, N. Keiser, R. Kalluri, H. Zeng, D. Mukhopadhyay, R. L. Chen, A. D. Lander, K. Hagihara, Y. Yamaguchi, R. Sasisekharan, L. Cantley, and V. P. Sukhatme Cell surface glypicans are low-affinity endostatin receptors *Mol Cell.* 7, 811-822 (2001)
13. K. Hagihara, K. Watanabe, J. Chun, and Y. Yamaguchi Glypican-4 is an FGF2-binding heparan sulfate proteoglycan expressed in neural precursor cells *Dev. Dyn.* 219, 353-367 (2000)
14. S. R. Farmer Transcriptional control of adipocyte formation *Cell Metab.* 4, 263-273 (2006)
15. Y. Y. Zhang, X. Li, S. W. Qian, L. Guo, H. Y. Huang, Q. He, Y. Liu, C. G. Ma, and Q. Q. Tang Transcriptional activation of histone H4 by C/EBP{beta} during the mitotic clonal expansion of 3T3-L1 adipocyte differentiation *Mol Biol Cell.* 22, 2165-2174 (2011)
16. B. H. Park, L. Qiang, and S. R. Farmer Phosphorylation of C/EBPbeta at a consensus extracellular signal-regulated kinase/glycogen synthase kinase 3 site is required for the induction of adiponectin gene expression during the differentiation of mouse fibroblasts into adipocytes *Mol Cell Biol.* 24, 8671-8680 (2004)
17. A. Traister, W. Shi, and J. Filmus Mammalian Notum induces the release of glypicans and other GPI-anchored proteins from the cell surface *Biochem. J.* Oct. 30, 2007)
18. N. Kloting, M. Fasshauer, A. Dietrich, P. Kovacs, M. R. Schon, M. Kern, M. Stumvoll, and M. Bluher Insulin-sensitive obesity *Am. J. Physiol Endocrinol. Metab.* 299, E506-E515 (2010)
19. S. M. Grundy Obesity, metabolic syndrome, and cardiovascular disease *J Clin Endocrinol Metab.* 89, 2595-2600 (2004)
20. G. Brunner, C. N. Metz, H. Nguyen, J. Gabrilove, S. R. Patel, M. A. Davitz, D. B. Rifkin, and E. L. Wilson An endogenous glycosylphosphatidylinositol-specific phospholipase D releases basic fibroblast growth factor-heparan sulfate proteoglycan complexes from human bone marrow cultures *Blood.* 83, 2115-2125 (Apr. 15, 1994)
21. N. S. Raikwar, R. F. Bowen-Deeg, X. S. Du, M. G. Low, and M. A. Deeg Glycosylphosphatidylinositol-specific phospholipase D improves glucose tolerance *Metabolism.* 59, 1413-1420 (2010)
22. A. R. Saltiel and P. Cuatrecasas In search of a second messenger for insulin *Am J Physiol.* 255, C1-11 (1988)
23. T. A. Kurtz, N. S. Fineberg, R. V. Considine, and M. A. Deeg Insulin resistance is associated with increased serum levels of glycosylphosphatidylinositol-specific phospholipase D *Metabolism.* 53, 138-139 (2004)
24. R. F. Bowen, N. S. Raikwar, L. K. Olson, and M. A. Deeg Glucose and insulin regulate glycosylphosphatidylinositol-specific phospholipase D expression in islet beta cells *Metabolism.* 50, 1489-1492 (2001)
25. J. F. Youngren Regulation of insulin receptor function *Cell Mol Life Sci.* 64, 873-891 (2007)
26. P. R. Srinivas, A. S. Wagner, L. V. Reddy, D. D. Deutsch, M. A. Leon, A. S. Goustin, and G. Grunberger Serum alpha 2-HS-glycoprotein is an inhibitor of the human insulin receptor at the tyrosine kinase level *Mol. Endocrinol.* 7, 1445-1455 (1993)
27. Q. Q. Tang, M. Gronborg, H. Huang, J. W. Kim, T. C. Otto, A. Pandey, and M. D. Lane Sequential phosphorylation of CCAAT enhancer-binding protein beta by MAPK and glycogen synthase kinase 3beta is required for adipogenesis *Proc Natl Acad Sci USA.* 102, 9766-9771 (Jul. 12, 2005)
28. H. Miki, T. Yamauchi, R. Suzuki, K. Komeda, A. Tsuchida, N. Kubota, Y. Terauchi, J. Kamon, Y. Kaburagi, J. Matsui, Y. Akanuma, R. Nagai, S. Kimura, K. Tobe, and T. Kadowaki Essential role of insulin receptor substrate 1 (IRS-1) and IRS-2 in adipocyte differentiation *Mol Cell Biol.* 21, 2521-2532 (2001)
29. O. Bezy, C. Vernochet, S. Gesta, S. R. Farmer, and C. R. Kahn TRB3 blocks adipocyte differentiation through the inhibition of C/EBPbeta transcriptional activity *Mol Cell Biol.* 27, 6818-6831 (2007)
30. J. Boucher, Y. H. Tseng, and C. R. Kahn Insulin and insulin-like growth factor-1 receptors act as ligand-specific amplitude modulators of a common pathway regulating gene transcription *J Biol Chem.* 285, 17235-17245 (May 28, 2010)

31. A. Woods and J. R. Couchman Proteoglycan isolation and analysis *Curr. Protoc. Cell Biol.* Chapter 10, Unit-2001)
32. C. Grunfeld, O. E. Van, F. A. Karlsson, and C. R. Kahn Antibody-induced desensitization of the insulin receptor. Studies of the mechanism of desensitization in 3T3-L1 fatty fibroblasts *J. Clin. Invest.* 66, 1124-1134 (1980)

TABLE 1

Multivariate regression analysis of Gpc4 WAT expression with clinical parameters

|  | Gpc4-SCF | Gpc4-Visc |
|---|---|---|
| Gpc4-SCF/Visc | −0.446 ± 0.124 | −0.183 ± 0.051 |
| GIR | 0.301 ± 0.167 | −0.367 ± 0.104 |
| FPG | −2.99 ± 10.453 | −2.754 ± 6.691 |
| FPI | −0.294 ± 0.454 | 0.093 ± 0.291 |
| HOMA-IR | 8.277 ± 12.882 | −3.807 ± 8.254 |
| HbA1c | −14.145 ± 12.424 | 2.03 ± 7.989 |
| WHR | −67.304 ± 26.343 | 23.974 ± 17.128 |
| BMI | −0.821 ± 0.668 | 0.707 ± 0.426 |
| FFA | 3.226 ± 11.273 | 4.479 ± 7.211 |
| Cholesterol | −3.451 ± 5.653 | −1.742 ± 3.622 |
| HDL-C | 10.937 ± 9.864 | −0.797 ± 6.343 |
| LDL-C | −5.614 ± 5.092 | −0.916 ± 3.273 |
| Gender | −10.416 ± 6.786 | 2.889 ± 4.374 |
| Age | 0.34 ± 0.201 | −0.44 ± 0.128 |

Shown are correlation coefficients±standard error. Values highlighted in bold indicate significant correlations with a p-value <0.05. SCF: subcutaneous fat; Visc: visceral fat.

TABLE 2

Multivariate regression analysis of serum Gpc4 with clinical parameters and Gpc4 expression in WAT

|  | serum Gpc4 |
|---|---|
| Gpc4-SCF | 0.004 ± 0.009 |
| Gpc4-Visc | −0.21 ± 0.014 |
| GIR | −0.46 ± 0.019 |
| FPG | −0.002 ± 1.164 |
| FPI | 0.0004788 ± 0.0515 |
| HOMA-IR | −0.59 ± 1.436 |
| HbA1c | 0.585 ± 1.389 |
| WHR | 3.023 ± 2.998 |
| BMI | 0.179 ± 0.075 |
| FFA | 0.895 ± 1.255 |
| Cholesterol | 0.217 ± 0.63 |
| HDL-C | 0.518 ± 1.103 |
| LDL-C | −0.996 ± −0.569 |
| Gender | 1.434 ± 0.762 |
| Age | 0.002 ± 0.022 |

Shown are correlation coefficients±standard error. Values highlighted in bold indicate significant correlations with a p-value <0.05. SCF: subcutaneous fat; Visc: visceral fat.

Supplementary Table 1. Shown are clinical parameters for female and male subjects, divided by BMI and body fat distribution used to measure adipose Gpc4 mRNA expression and serum Gpc4 levels. visc. BMI 25-30 and visc. BMI >30 indicates subjects with a CT or MRI ratio between subcutaneous and visceral fat areas >0.4 in the given BMI range.

| Group | BMI <25 | | BMI 25-30 | | Visc. BMI 25-30 | | BMI >30 | | Visc. BMI >30 | |
|---|---|---|---|---|---|---|---|---|---|---|
| Female | | | | | | | | | | |
| BMI (kg/m$^2$) | 23.3 | ±1.1 | 27.7 | ±1.6 | 27.1 | ±1.0 | 36.0 | ±4.9 | 37.4 | ±5.7 |
| WHR | 0.7 | ±0.1 | 0.9 | ±0.1 | 1.0 | ±0.1 | 1.0 | ±0.2 | 1.2 | ±0.1 |
| % body fat | 21.7 | ±2.8 | 30.6 | ±6.2 | 26.5 | ±3.2 | 40.2 | ±6.9 | 36.0 | ±7.9 |
| FPG (mmol/l) | 5.3 | ±0.4 | 5.3 | ±0.6 | 5.1 | ±0.6 | 5.4 | ±0.4 | 5.4 | ±0.3 |
| FPI (pmol/l) | 27.5 | ±12.6 | 97.0 | ±65.6 | 74.3 | ±16.1 | 153.0 | ±95.4 | 152.9 | ±78.8 |
| Clamp GIR (μmol/kg/min) | 97.4 | ±10.5 | 59.1 | ±25.3 | 54.3 | ±24.9 | 53.9 | ±24.1 | 47.6 | ±33.7 |
| HbA1c (%) | 5.3 | ±0.2 | 5.4 | ±0.2 | 5.6 | ±0.2 | 5.5 | ±0.3 | 5.5 | ±0.3 |
| Cholesterol (mmol/l) | 5.0 | ±0.8 | 4.7 | ±0.6 | 5.4 | ±0.5 | 4.9 | ±0.7 | 5.7 | ±0.7 |
| HDL-C (mmol/l) | 1.5 | ±0.5 | 1.3 | ±0.4 | 1.6 | ±0.5 | 1.4 | ±0.4 | 1.6 | ±0.3 |
| LDL-C (mmol/l) | 2.9 | ±0.9 | 2.6 | ±0.5 | 3.5 | ±0.5 | 2.7 | ±0.6 | 3.4 | ±0.5 |
| FFA (mmol/l) | 0.3 | ±0.1 | 0.4 | ±0.3 | 0.6 | ±0.1 | 0.6 | ±0.4 | 0.9 | ±0.2 |
| Leptin (ng/ml) | 8.7 | ±4.3 | 26.8 | ±10.8 | 35.6 | ±15.4 | 33.0 | ±11.2 | 31.5 | ±7.9 |
| Adiponectin (ng/ml) | 9.7 | ±4.5 | 8.4 | ±5.1 | 3.4 | ±1.9 | 7.4 | ±4.3 | 5.9 | ±3.3 |
| Male | | | | | | | | | | |
| BMI (kg/m$^2$) | 23.9 | ±0.9 | 26.8 | ±1.7 | 28.0 | ±1.3 | 37.1 | ±5.0 | 35.9 | ±5.7 |
| WHR | 0.9 | ±0.1 | 1.0 | ±0.1 | 1.1 | ±0.1 | 1.1 | ±0.1 | 1.2 | ±0.1 |
| % body fat | 21.3 | ±2.7 | 26.6 | ±6.7 | 30.3 | ±3.3 | 42.5 | ±8.8 | 34.5 | ±5.8 |
| FPG (mmol/l) | 5.4 | ±0.4 | 5.4 | ±0.5 | 5.2 | ±0.4 | 5.4 | ±0.5 | 5.5 | ±0.5 |
| FPI (pmol/l) | 31.5 | ±14.9 | 72.7 | ±90.6 | 203.5 | ±81.4 | 146.0 | ±113.9 | 128.8 | ±56.3 |
| Clamp GIR (μmol/kg/min) | 96.8 | ±5.5 | 85.6 | ±24.1 | 30.8 | ±12.9 | 59.0 | ±26.2 | 47.3 | ±31.1 |
| HbA1c (%) | 5.3 | ±0.2 | 5.4 | ±0.3 | 5.6 | ±0.2 | 5.6 | ±0.2 | 5.6 | ±0.3 |
| Cholesterol (mmol/l) | 5.1 | ±0.8 | 4.8 | ±0.7 | 5.6 | ±0.5 | 4.8 | ±0.5 | 5.5 | ±1.0 |
| HDL-C (mmol/l) | 1.4 | ±0.4 | 1.4 | ±0.3 | 1.8 | ±0.4 | 1.3 | ±0.3 | 1.4 | ±0.2 |
| LDL-C (mmol/l) | 2.7 | ±0.7 | 2.5 | ±0.5 | 3.1 | ±0.4 | 2.7 | ±0.6 | 3.6 | ±1.1 |
| FFA (mmol/l) | 0.3 | ±0.2 | 0.4 | ±0.2 | 0.7 | ±0.3 | 0.6 | ±0.4 | 0.7 | ±0.4 |
| Leptin (ng/ml) | 3.2 | ±2.9 | 9.6 | ±11.8 | 22.1 | ±9.7 | 19.3 | ±8.3 | 16.6 | ±9.9 |
| Adiponectin (ng/ml) | 9.7 | ±2.5 | 9.2 | ±6.7 | 4.3 | ±3.6 | 6.1 | ±2.6 | 4.3 | ±2.0 |

We claim:

1. A method for increasing insulin sensitivity in a subject, comprising administering to a subject in need of increased insulin sensitivity a therapeutically effective amount of a glypican-4 agent, wherein the glypican-4 agent is a peptide consisting of SEQ ID NO: 3, or a peptide comprising amino acids 7-537 of SEQ ID NO: 11.

2. The method of claim 1, wherein the subject is insulin resistant.

3. The method of claim 1, wherein the subject has metabolic syndrome.

4. The method of claim 1, wherein the subject has type 2 diabetes.

5. The method of claim 1, wherein the glypican-4 agent is a peptide consisting of SEQ ID NO: 3.

6. The method of claim 1, wherein the glypican-4 protein comprises a glycosylphosphatidylinositol (GPI) anchor.

7. The method of claim 1, wherein the glypican-4 protein is a soluble protein.

8. The method of claim 1, wherein the glypican-4 agent is administered systemically.

9. The method of claim 1, wherein the glypican-4 agent is administered into adipose tissue.

10. The method of claim 1, wherein the glypican-4 agent is a peptide comprising amino acids 7-537 of SEQ ID NO: 11.

* * * * *

SEQUENCE LISTING

<160> NUMBER OF SEQ ID NOS: 11

<210> SEQ ID NO 1
<211> LENGTH: 3714
<212> TYPE: DNA
<213> ORGANISM: Homo sapiens

<400> SEQUENCE: 1

| | | | | | | |
|---|---|---|---|---|---|---|
| gcctggcacc | ggggaccgtt | gcctgacgcg | aggcccagct | ctactttcg | ccccgcgtct | 60 |
| cctccgcctg | ctcgcctctt | ccaccaactc | caactccttc | tccctccagc | tccactcgct | 120 |
| agtccccgac | tccgccagcc | ctcggcccgc | tgccgtagcg | ccgcttcccg | tccggtccca | 180 |
| aaggtgggaa | cgcgtccgcc | ccggcccgca | ccatggcacg | gttcggcttg | cccgcgcttc | 240 |
| tctgcaccct | ggcagtgctc | agcgccgcgc | tgctggctgc | cgagctcaag | tcgaaaagtt | 300 |
| gctcggaagt | gcgacgtctt | tacgtgtcca | aaggcttcaa | caagaacgat | gccccctcc | 360 |
| acgagatcaa | cggtgatcat | ttgaagatct | gtccccaggg | ttctacctgc | tgctctcaag | 420 |
| agatggagga | gaagtacagc | ctgcaaagta | aagatgattt | caaaagtgtg | gtcagcgaac | 480 |
| agtgcaatca | tttgcaagct | gtcttgctt | cacgttacaa | gaagtttgat | gaattcttca | 540 |
| aagaactact | tgaaaatgca | gagaaatccc | tgaatgatat | gtttgtgaag | acatatggcc | 600 |
| atttatacat | gcaaaattct | gagctattta | agatctctt | cgtagagttg | aaacgttact | 660 |
| acgtggtggg | aaatgtgaac | ctggaagaaa | tgctaaatga | cttctgggct | cgcctcctgg | 720 |
| agcggatgtt | ccgcctggtg | aactcccagt | accactttac | agatgagtat | ctggaatgtg | 780 |
| tgagcaagta | tacggagcag | ctgaagccct | tcggagatgt | ccctcgcaaa | ttgaagctcc | 840 |
| aggttactcg | tgcttttgta | gcagcccgta | ctttcgctca | aggcttagcg | gttgcgggag | 900 |
| atgtcgtgag | caaggtctcc | gtggtaaacc | ccacagccca | gtgtacccat | gccctgttga | 960 |
| agatgatcta | ctgctcccac | tgccggggtc | tcgtgactgt | gaagccatgt | acaactact | 1020 |
| gctcaaacat | catgagaggc | tgtttggcca | accaagggga | tctcgatttt | gaatggaaca | 1080 |
| atttcataga | tgctatgctg | atggtggcag | agaggctaga | gggtccttc | aacattgaat | 1140 |
| cggtcatgga | tccatcgat | gtgaagattt | ctgatgctat | tatgaacatg | caggataata | 1200 |
| gtgttcaagt | gtctcagaag | gttttccagg | gatgtggacc | cccaagccc | ctcccagctg | 1260 |
| gacgaattc | tcgttccatc | tctgaaagtg | ccttcagtgc | tcgcttcaga | ccacatcacc | 1320 |
| ccgaggaacg | cccaaccaca | gcagctggca | ctagtttgga | ccgactggtt | actgatgtca | 1380 |
| aggagaaact | gaaacaggcc | aagaaattct | ggtcctccct | tccgagcaac | gtttgcaacg | 1440 |
| atgagaggat | ggctgcagga | aacggcaatg | aggatgactg | ttggaatggg | aaaggcaaaa | 1500 |
| gcaggtacct | gtttgcagtg | acaggaaatg | gattagccaa | ccagggcaac | aacccagagg | 1560 |
| tccaggttga | caccagcaaa | ccagacatac | tgatccttcg | tcaaatcatg | gctcttcgag | 1620 |
| tgatgaccag | caagatgaag | aatgcataca | atgggaacga | cgtggacttc | tttgatatca | 1680 |
| gtgatgaaag | tagtggagaa | ggaagtggaa | gtggctgtga | gtatcagcag | tgcccttcag | 1740 |
| agtttgacta | caatgccact | gaccatgctg | ggaagagtgc | caatgagaaa | gccgacagtg | 1800 |
| ctggtgtccg | tcctgggca | caggcctacc | tcctcactgt | cttctgcatc | ttgttcctgg | 1860 |
| ttatgcagag | agagtggaga | taattctcaa | actctgaaga | aaagtgttca | tcaaaaagtt | 1920 |
| aaaaggcacc | agttatcact | tttctaccat | cctagtgact | tgctttta | aatgaatgga | 1980 |
| caacaatgta | cagttttac | tatgtggcca | ctggtttaag | aagtgctgac | tttgttttct | 2040 |
| cattcagttt | tgggaggaaa | agggactgtg | cattgagttg | gttcctgctc | ccccaaacca | 2100 |

-continued

```
tgttaaacgt ggctaacagt gtaggtacag aactatagtt agttgtgcat ttgtgatttt    2160
atcactctat tatttgtttg tatgttttt tctcatttcg tttgtgggtt ttttttttcca    2220
actgtgatct cgccttgttt cttacaagca aaccagggtc ccttcttggc acgtaacatg    2280
tacgtatttc tgaaatatta aatagctgta cagaagcagg ttttatttat catgttatct    2340
tattaaaaga aaaagcccaa aaagcagtaa aatttccatt tctccctgtt attttagttg    2400
ccttatctgg agagacgtgg aggtgatttt cttttttta aattattatt aagcacagaat   2460
gtgagggcac aagcaggctt ctgagccact tgtcagattg tattcaaagc atcaatccaa    2520
gaaggaggtt atgtgtactt catttattgg tgatagttgg aagagactgc agactactgc    2580
tttgaatgag ttgaattaca taagctaaga tcactatagg tccatttctt gaacccactt    2640
atacataaaa tgtaacccat ttagaaaaag attctggata tcatcccct tgaaagatag     2700
aaagcattca ggatgtccca gttatcacat gttcacactt gggtttaggg gtgtttttt     2760
ttaaaaccag gcaggttagc tagcccaccc tgtgctagtt ttcatgttca cactgaccct    2820
atttgaatta atatcctttg ttagagtggt cgagatttca aacccaatta tgtacaggga    2880
gctgtctgag agctagccag aactggggta cagcctgggc tcaggaata gctgtcaaca     2940
ctcgggcaaa gttttttgtct gtgcatgtgt atctccattt gttttgggat cccagttttt   3000
gttttaagag agtataaggt gtctcatttg agtctttttc ttacctagcc ccctcttatc    3060
agtaaaacaa aggacttgcc atggttcaca gcaatgtgct acgatccaag atatcagcca    3120
aggagcccac ttaggggaga actaggtgtc cagatttttg tatgtgttgt ttttcttggg    3180
ggatggggtg gggtgggagt aggtagagct gagaatacta catcttagtg gtgacccttta  3240
gccacgtggg tgaagtggca aaggccatgg ccatatctgt tgtcccaggc caaagactaa    3300
caactgcctt gggaatccct tccttgtgtc cttaccaaat gatagctcat aaaactctga    3360
taatgtaaca aatcactttc aaaggagttc ccagaagtct tcagaaagac taaaattctg    3420
tctcttcctg ctttagacag ccattaagat cccaactaat tttaccgaac ctaaaaccca    3480
caaagaggtt gtttgtgtta ttgttcaatc ttcagttgta agagtaattc tctatttta     3540
tattgaaaca taattacttg atagctcagg gtctacattt cattcaactt tttacaccaa    3600
attctgcaga gtggtcaaaa tggaatattg ggggctgttg taaacagagg cttaattta     3660
ttagaagtag ccagttattt attaaagcat gatgttaata aaataggcat attc           3714
```

<210> SEQ ID NO 2
<211> LENGTH: 556
<212> TYPE: PRT
<213> ORGANISM: Homo sapiens

<400> SEQUENCE: 2

Met Ala Arg Phe Gly Leu Pro Ala Leu Leu Cys Thr Leu Ala Val Leu
1               5                   10                  15

Ser Ala Ala Leu Leu Ala Ala Glu Leu Lys Ser Lys Ser Cys Ser Glu
                20                  25                  30

Val Arg Arg Leu Tyr Val Ser Lys Gly Phe Asn Lys Asn Asp Ala Pro
            35                  40                  45

Leu His Glu Ile Asn Gly Asp His Leu Lys Ile Cys Pro Gln Gly Ser
        50                  55                  60

Thr Cys Cys Ser Gln Glu Met Glu Glu Lys Tyr Ser Leu Gln Ser Lys
65                  70                  75                  80

Asp Asp Phe Lys Ser Val Val Ser Glu Gln Cys Asn His Leu Gln Ala

```
                85                  90                  95
Val Phe Ala Ser Arg Tyr Lys Lys Phe Asp Glu Phe Lys Glu Leu
            100                 105                 110
Leu Glu Asn Ala Glu Lys Ser Leu Asn Asp Met Phe Lys Thr Tyr
            115                 120                 125
Gly His Leu Tyr Met Gln Asn Ser Glu Leu Phe Lys Asp Leu Phe Val
        130                 135                 140
Glu Leu Lys Arg Tyr Tyr Val Gly Asn Val Asn Leu Glu Met
145                 150                 155                 160
Leu Asn Asp Phe Trp Ala Arg Leu Leu Glu Arg Met Phe Arg Leu Val
                165                 170                 175
Asn Ser Gln Tyr His Phe Thr Asp Glu Tyr Leu Glu Cys Val Ser Lys
            180                 185                 190
Tyr Thr Glu Gln Leu Lys Pro Phe Gly Asp Val Pro Arg Lys Leu Lys
            195                 200                 205
Leu Gln Val Thr Arg Ala Phe Val Ala Arg Thr Phe Ala Gln Gly
        210                 215                 220
Leu Ala Val Ala Gly Asp Val Val Ser Lys Val Ser Val Val Asn Pro
225                 230                 235                 240
Thr Ala Gln Cys Thr His Ala Leu Leu Lys Met Ile Tyr Cys Ser His
                245                 250                 255
Cys Arg Gly Leu Val Thr Val Lys Pro Cys Tyr Asn Tyr Cys Ser Asn
            260                 265                 270
Ile Met Arg Gly Cys Leu Ala Asn Gln Gly Asp Leu Asp Phe Glu Trp
            275                 280                 285
Asn Asn Phe Ile Asp Ala Met Leu Met Val Ala Glu Arg Leu Glu Gly
        290                 295                 300
Pro Phe Asn Ile Glu Ser Val Met Asp Pro Ile Asp Val Lys Ile Ser
305                 310                 315                 320
Asp Ala Ile Met Asn Met Gln Asp Asn Ser Val Gln Val Ser Gln Lys
                325                 330                 335
Val Phe Gln Gly Cys Gly Pro Pro Lys Pro Leu Pro Ala Gly Arg Ile
            340                 345                 350
Ser Arg Ser Ile Ser Glu Ser Ala Phe Ser Ala Arg Phe Arg Pro His
            355                 360                 365
His Pro Glu Glu Arg Pro Thr Thr Ala Ala Gly Thr Ser Leu Asp Arg
        370                 375                 380
Leu Val Thr Asp Val Lys Glu Lys Leu Lys Gln Ala Lys Lys Phe Trp
385                 390                 395                 400
Ser Ser Leu Pro Ser Asn Val Cys Asn Asp Glu Arg Met Ala Ala Gly
                405                 410                 415
Asn Gly Asn Glu Asp Asp Cys Trp Asn Gly Lys Gly Lys Ser Arg Tyr
            420                 425                 430
Leu Phe Ala Val Thr Gly Asn Gly Leu Ala Asn Gln Gly Asn Asn Pro
            435                 440                 445
Glu Val Gln Val Asp Thr Ser Lys Pro Asp Ile Leu Ile Leu Arg Gln
        450                 455                 460
Ile Met Ala Leu Arg Val Met Thr Ser Lys Met Lys Asn Ala Tyr Asn
465                 470                 475                 480
Gly Asn Asp Val Asp Phe Phe Asp Ile Ser Asp Glu Ser Ser Gly Glu
                485                 490                 495
Gly Ser Gly Ser Gly Cys Glu Tyr Gln Gln Cys Pro Ser Glu Phe Asp
            500                 505                 510
```

```
Tyr Asn Ala Thr Asp His Ala Gly Lys Ser Ala Asn Glu Lys Ala Asp
            515                 520                 525

Ser Ala Gly Val Arg Pro Gly Ala Gln Ala Tyr Leu Leu Thr Val Phe
530                 535                 540

Cys Ile Leu Phe Leu Val Met Gln Arg Glu Trp Arg
545                 550                 555

<210> SEQ ID NO 3
<211> LENGTH: 534
<212> TYPE: PRT
<213> ORGANISM: Homo sapiens

<400> SEQUENCE: 3

Ala Glu Leu Lys Ser Lys Ser Cys Ser Glu Val Arg Arg Leu Tyr Val
1               5                   10                  15

Ser Lys Gly Phe Asn Lys Asn Asp Ala Pro Leu His Glu Ile Asn Gly
            20                  25                  30

Asp His Leu Lys Ile Cys Pro Gln Gly Ser Thr Cys Cys Ser Gln Glu
        35                  40                  45

Met Glu Glu Lys Tyr Ser Leu Gln Ser Lys Asp Asp Phe Lys Ser Val
50                  55                  60

Val Ser Glu Gln Cys Asn His Leu Gln Ala Val Phe Ala Ser Arg Tyr
65                  70                  75                  80

Lys Lys Phe Asp Glu Phe Phe Lys Glu Leu Leu Glu Asn Ala Glu Lys
                85                  90                  95

Ser Leu Asn Asp Met Phe Val Lys Thr Tyr Gly His Leu Tyr Met Gln
            100                 105                 110

Asn Ser Glu Leu Phe Lys Asp Leu Phe Val Glu Leu Lys Arg Tyr Tyr
        115                 120                 125

Val Val Gly Asn Val Asn Leu Glu Glu Met Leu Asn Asp Phe Trp Ala
130                 135                 140

Arg Leu Leu Glu Arg Met Phe Arg Leu Val Asn Ser Gln Tyr His Phe
145                 150                 155                 160

Thr Asp Glu Tyr Leu Glu Cys Val Ser Lys Tyr Thr Glu Gln Leu Lys
                165                 170                 175

Pro Phe Gly Asp Val Pro Arg Lys Leu Lys Leu Gln Val Thr Arg Ala
            180                 185                 190

Phe Val Ala Ala Arg Thr Phe Ala Gln Gly Leu Ala Val Ala Gly Asp
        195                 200                 205

Val Val Ser Lys Val Ser Val Val Asn Pro Thr Ala Gln Cys Thr His
210                 215                 220

Ala Leu Leu Lys Met Ile Tyr Cys Ser His Cys Arg Gly Leu Val Thr
225                 230                 235                 240

Val Lys Pro Cys Tyr Asn Tyr Cys Ser Asn Ile Met Arg Gly Cys Leu
                245                 250                 255

Ala Asn Gln Gly Asp Leu Asp Phe Glu Trp Asn Asn Phe Ile Asp Ala
            260                 265                 270

Met Leu Met Val Ala Glu Arg Leu Glu Gly Pro Phe Asn Ile Glu Ser
        275                 280                 285

Val Met Asp Pro Ile Asp Val Lys Ile Ser Asp Ala Ile Met Asn Met
290                 295                 300

Gln Asp Asn Ser Val Gln Val Ser Gln Lys Val Phe Gln Gly Cys Gly
305                 310                 315                 320

Pro Pro Lys Pro Leu Pro Ala Gly Arg Ile Ser Arg Ser Ile Ser Glu
```

|  |  |  | 325 |  |  |  | 330 |  |  |  | 335 |  |  |
|--|--|--|--|--|--|--|--|--|--|--|--|--|--|

Ser Ala Phe Ser Ala Arg Phe Arg Pro His His Pro Glu Glu Arg Pro
                340                 345                 350

Thr Thr Ala Ala Gly Thr Ser Leu Asp Arg Leu Val Thr Asp Val Lys
            355                 360                 365

Glu Lys Leu Lys Gln Ala Lys Lys Phe Trp Ser Ser Leu Pro Ser Asn
    370                 375                 380

Val Cys Asn Asp Glu Arg Met Ala Ala Gly Asn Gly Asn Glu Asp Asp
385                 390                 395                 400

Cys Trp Asn Gly Lys Gly Lys Ser Arg Tyr Leu Phe Ala Val Thr Gly
                405                 410                 415

Asn Gly Leu Ala Asn Gln Gly Asn Asn Pro Glu Val Gln Val Asp Thr
            420                 425                 430

Ser Lys Pro Asp Ile Leu Ile Leu Arg Gln Ile Met Ala Leu Arg Val
        435                 440                 445

Met Thr Ser Lys Met Lys Asn Ala Tyr Asn Gly Asn Asp Val Asp Phe
    450                 455                 460

Phe Asp Ile Ser Asp Glu Ser Ser Gly Glu Gly Ser Gly Ser Gly Cys
465                 470                 475                 480

Glu Tyr Gln Gln Cys Pro Ser Glu Phe Asp Tyr Asn Ala Thr Asp His
                485                 490                 495

Ala Gly Lys Ser Ala Asn Glu Lys Ala Asp Ser Ala Gly Val Arg Pro
            500                 505                 510

Gly Ala Gln Ala Tyr Leu Leu Thr Val Phe Cys Ile Leu Phe Leu Val
        515                 520                 525

Met Gln Arg Glu Trp Arg
    530

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgagaaagct gaccaccatc accatcacca tggtgcccat gcag                    44

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctgcatgggc accatggtga tggtgatggt ggtcagcttt ctcg                    44

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gccactggtt taagcaatgt t                                             21

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aggttaagtc gccctcg                                                        17

<210> SEQ ID NO 8
<211> LENGTH: 20
<212> TYPE: PRT
<213> ORGANISM: Mus sp.

<400> SEQUENCE: 8

Glu Val Arg Arg Leu Tyr Val Ser Lys Gly Phe Asn Lys Asn Asp Ala
1               5                   10                  15

Pro Leu Tyr Glu
            20

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
1               5

<210> SEQ ID NO 10
<211> LENGTH: 557
<212> TYPE: PRT
<213> ORGANISM: Mus sp.

<400> SEQUENCE: 10

Met Ala Arg Leu Gly Leu Leu Ala Leu Leu Cys Thr Leu Ala Ala Leu
1               5                   10                  15

Ser Ala Ser Leu Leu Ala Ala Glu Leu Lys Ser Lys Ser Cys Ser Glu
                20                  25                  30

Val Arg Arg Leu Tyr Val Ser Lys Gly Phe Asn Lys Asn Asp Ala Pro
            35                  40                  45

Leu Tyr Glu Ile Asn Gly Asp His Leu Lys Ile Cys Pro Gln Asp Tyr
        50                  55                  60

Thr Cys Cys Ser Gln Glu Met Glu Glu Lys Tyr Ser Leu Gln Ser Lys
65                  70                  75                  80

Asp Asp Phe Lys Thr Val Val Ser Glu Gln Cys Asn His Leu Gln Ala
                85                  90                  95

Ile Phe Ala Ser Arg Tyr Lys Lys Phe Asp Glu Phe Lys Glu Leu
            100                 105                 110

Leu Glu Asn Ala Glu Lys Ser Leu Asn Asp Met Phe Val Lys Thr Tyr
            115                 120                 125

Gly His Leu Tyr Met Gln Asn Ser Glu Leu Phe Lys Asp Leu Phe Val
        130                 135                 140

Glu Leu Lys Arg Tyr Tyr Val Ala Gly Asn Val Asn Leu Glu Glu Met
145                 150                 155                 160

Leu Asn Asp Phe Trp Ala Arg Leu Leu Glu Arg Met Phe Arg Leu Val
            165                 170                 175

Asn Ser Gln Tyr His Phe Thr Asp Glu Tyr Leu Glu Cys Val Ser Lys
            180                 185                 190

Tyr Thr Glu Gln Leu Lys Pro Phe Gly Asp Val Pro Arg Lys Leu Lys
            195                 200                 205

Leu Gln Val Thr Arg Ala Phe Val Ala Ala Arg Thr Phe Ala Gln Gly
            210                 215                 220

Leu Ala Val Ala Arg Asp Val Val Ser Lys Val Ser Val Val Asn Pro
225                 230                 235                 240

Thr Ala Gln Cys Thr His Ala Leu Leu Lys Met Ile Tyr Cys Ser His
            245                 250                 255

Cys Arg Gly Leu Val Thr Val Lys Pro Cys Tyr Asn Tyr Cys Ser Asn
            260                 265                 270

Ile Met Arg Gly Cys Leu Ala Asn Gln Gly Asp Leu Asp Phe Glu Trp
            275                 280                 285

Asn Asn Phe Ile Asp Ala Met Leu Met Val Ala Glu Arg Leu Glu Gly
            290                 295                 300

Pro Phe Asn Ile Glu Ser Val Met Asp Pro Ile Asp Val Lys Ile Ser
305                 310                 315                 320

Asp Ala Ile Met Asn Met Gln Asp Asn Ser Val Gln Val Ser Gln Lys
            325                 330                 335

Val Phe Gln Gly Cys Gly Pro Pro Lys Pro Leu Pro Ala Gly Arg Ile
            340                 345                 350

Ser Arg Ser Ile Ser Glu Ser Ala Phe Ser Ala Arg Phe Arg Pro Tyr
            355                 360                 365

His Pro Glu Gln Arg Pro Thr Thr Ala Gly Thr Ser Leu Asp Arg
            370                 375                 380

Leu Val Thr Asp Val Lys Glu Lys Leu Lys Gln Ala Lys Lys Phe Trp
385                 390                 395                 400

Ser Ser Leu Pro Ser Thr Val Cys Asn Asp Glu Arg Met Ala Ala Gly
            405                 410                 415

Asn Glu Asn Glu Asp Asp Cys Trp Asn Gly Lys Gly Lys Ser Arg Tyr
            420                 425                 430

Leu Phe Ala Val Thr Gly Asn Gly Leu Ala Asn Gln Gly Asn Asn Pro
            435                 440                 445

Glu Val Gln Val Asp Thr Ser Lys Pro Asp Ile Leu Ile Leu Arg Gln
450                 455                 460

Ile Met Ala Leu Arg Val Met Thr Ser Lys Met Lys Asn Ala Tyr Asn
465                 470                 475                 480

Gly Asn Asp Val Asp Phe Phe Asp Ile Ser Asp Glu Ser Ser Gly Glu
            485                 490                 495

Gly Ser Gly Ser Gly Cys Glu Tyr Gln Gln Cys Pro Ser Glu Phe Glu
            500                 505                 510

Tyr Asn Ala Thr Asp His Ser Gly Lys Ser Ala Asn Glu Lys Ala Asp
            515                 520                 525

Ser Ala Gly Gly Ala His Ala Glu Ala Lys Pro Tyr Leu Leu Ala Ala
530                 535                 540

Leu Cys Ile Leu Phe Leu Ala Val Gln Gly Glu Trp Arg
545                 550                 555

<210> SEQ ID NO 11
<211> LENGTH: 537

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

His His His His His Ala Glu Leu Lys Ser Lys Ser Cys Ser Glu
1               5                   10                  15

Val Arg Arg Leu Tyr Val Ser Lys Gly Phe Asn Lys Asn Asp Ala Pro
            20                  25                  30

Leu His Glu Ile Asn Gly Asp His Leu Lys Ile Cys Pro Gln Gly Ser
        35                  40                  45

Thr Cys Cys Ser Gln Glu Met Glu Glu Lys Tyr Ser Leu Gln Ser Lys
    50                  55                  60

Asp Asp Phe Lys Ser Val Val Ser Glu Gln Cys Asn His Leu Gln Ala
65                  70                  75                  80

Val Phe Ala Ser Arg Tyr Lys Lys Phe Asp Glu Phe Lys Glu Leu
                85                  90                  95

Leu Glu Asn Ala Glu Lys Ser Leu Asn Asp Met Phe Val Lys Thr Tyr
            100                 105                 110

Gly His Leu Tyr Met Gln Asn Ser Glu Leu Phe Lys Asp Leu Phe Val
        115                 120                 125

Glu Leu Lys Arg Tyr Tyr Val Val Gly Asn Val Asn Leu Glu Glu Met
130                 135                 140

Leu Asn Asp Phe Trp Ala Arg Leu Leu Glu Arg Met Phe Arg Leu Val
145                 150                 155                 160

Asn Ser Gln Tyr His Phe Thr Asp Glu Tyr Leu Glu Cys Val Ser Lys
                165                 170                 175

Tyr Thr Glu Gln Leu Lys Pro Phe Gly Asp Val Pro Arg Lys Leu Lys
            180                 185                 190

Leu Gln Val Thr Arg Ala Phe Val Ala Ala Arg Thr Phe Ala Gln Gly
        195                 200                 205

Leu Ala Val Ala Gly Asp Val Val Ser Lys Val Ser Val Val Asn Pro
210                 215                 220

Thr Ala Gln Cys Thr His Ala Leu Leu Lys Met Ile Tyr Cys Ser His
225                 230                 235                 240

Cys Arg Gly Leu Val Thr Val Lys Pro Cys Tyr Asn Tyr Cys Ser Asn
                245                 250                 255

Ile Met Arg Gly Cys Leu Ala Asn Gln Gly Asp Leu Asp Phe Glu Trp
            260                 265                 270

Asn Asn Phe Ile Asp Ala Met Leu Met Val Ala Glu Arg Leu Glu Gly
        275                 280                 285

Pro Phe Asn Ile Glu Ser Val Met Asp Pro Ile Asp Val Lys Ile Ser
290                 295                 300

Asp Ala Ile Met Asn Met Gln Asp Asn Ser Val Gln Val Ser Gln Lys
305                 310                 315                 320

Val Phe Gln Gly Cys Gly Pro Pro Lys Pro Leu Pro Ala Gly Arg Ile
                325                 330                 335

Ser Arg Ser Ile Ser Glu Ser Ala Phe Ser Ala Arg Phe Arg Pro His
            340                 345                 350

His Pro Glu Glu Arg Pro Thr Thr Ala Ala Gly Thr Ser Leu Asp Arg
        355                 360                 365

Leu Val Thr Asp Val Lys Glu Lys Leu Lys Gln Ala Lys Lys Phe Trp
370                 375                 380

```
Ser Ser Leu Pro Ser Asn Val Cys Asn Asp Glu Arg Met Ala Ala Gly
385                 390                 395                 400

Asn Gly Asn Glu Asp Asp Cys Trp Asn Gly Lys Gly Lys Ser Arg Tyr
                405                 410                 415

Leu Phe Ala Val Thr Gly Asn Gly Leu Ala Asn Gln Gly Asn Asn Pro
                420                 425                 430

Glu Val Gln Val Asp Thr Ser Lys Pro Asp Ile Leu Ile Leu Arg Gln
            435                 440                 445

Ile Met Ala Leu Arg Val Met Thr Ser Lys Met Lys Asn Ala Tyr Asn
        450                 455                 460

Gly Asn Asp Val Asp Phe Phe Asp Ile Ser Asp Glu Ser Ser Gly Glu
465                 470                 475                 480

Gly Ser Gly Ser Gly Cys Glu Tyr Gln Gln Cys Pro Ser Glu Phe Asp
                485                 490                 495

Tyr Asn Ala Thr Asp His Ala Gly Lys Ser Ala Asn Glu Lys Ala Asp
                500                 505                 510

Val Arg Pro Gly Ala Gln Ala Tyr Leu Leu Thr Val Phe Cys Ile Leu
        515                 520                 525

Phe Leu Val Met Gln Arg Glu Trp Arg
        530                 535
```